(12) United States Patent
Hurson

(10) Patent No.: US 6,769,913 B2
(45) Date of Patent: Aug. 3, 2004

(54) IMPRESSION CAP

(75) Inventor: Steven M. Hurson, Yorba Linda, CA (US)

(73) Assignee: Nobel Biocare AB, Gothenburg (SE)

( * ) Notice: Subject to any disclaimer, the term of this patent is extended or adjusted under 35 U.S.C. 154(b) by 89 days.

(21) Appl. No.: 09/945,158

(22) Filed: Aug. 30, 2001

(65) Prior Publication Data

US 2002/0106610 A1 Aug. 8, 2002

Related U.S. Application Data

(60) Provisional application No. 60/229,114, filed on Aug. 30, 2000.

(51) Int. Cl.[7] .................................................. A61C 8/00
(52) U.S. Cl. ........................ 433/173; 433/172; 433/214
(58) Field of Search ................................. 433/172, 173, 433/174, 175, 176, 214

(56) References Cited

U.S. PATENT DOCUMENTS

| | | | |
|---|---|---|---|
| 3,304,608 A | 2/1967 | Frohnecke | 433/40 |
| 4,483,675 A | 11/1984 | Marshall | 433/141 |
| 4,763,788 A | 8/1988 | Jorneus et al. | 206/438 |
| 5,026,285 A | 6/1991 | Durr et al. | 433/173 |
| 5,125,841 A | 6/1992 | Carlsson et al. | 433/213 |
| 5,195,891 A | 3/1993 | Sulc | 433/173 |
| 5,213,498 A | 5/1993 | Pelerin | 433/37 |
| 5,259,759 A | 11/1993 | Jorneus et al. | 433/173 |
| 5,302,125 A | 4/1994 | Xownacki et al. | 433/172 |
| 5,368,483 A | 11/1994 | Sutter et al. | 433/173 |
| 5,417,570 A | 5/1995 | Zuest et al. | 433/177 |
| 5,674,073 A | 10/1997 | Ingber et al. | 433/213 |
| 5,685,715 A | 11/1997 | Beaty et al. | 433/173 |
| 5,688,123 A | 11/1997 | Meiers et al. | 433/173 |
| 5,829,981 A | 11/1998 | Ziegler | 433/214 |
| 5,899,695 A | 5/1999 | Lazzara et al. | 433/172 |
| 5,938,443 A | 8/1999 | Lazzara et al. | 433/173 |
| 6,068,478 A | 5/2000 | Grande et al. | 433/172 |
| 6,488,501 B1 * | 12/2002 | Harding | 433/173 |

FOREIGN PATENT DOCUMENTS

| | | |
|---|---|---|
| DE | 1 232 314 | 3/1963 |
| DE | 1 541 225 | 10/1966 |
| DE | 197 42 381 A1 | 9/1997 |
| EP | 0 879 025 B1 | 1/1997 |
| WO | WO 97/28756 | 1/1997 |

* cited by examiner

*Primary Examiner*—John J. Wilson
(74) *Attorney, Agent, or Firm*—Knobbe, Martens, Olson & Bear, LLP.

(57) ABSTRACT

An impression cap for taking dental impressions in a patient's mouth comprises a distal end that includes a top surface and a proximal end that defines an opening. The impression cap also includes an inner surface that defines an internal cavity. The proximal end of the impression cap is configured to engage a corresponding shoulder of a prosthetic abutment in a snap fit. The impression cap further comprises an injection port configured to receive a tip of an injection syringe for injecting impression material under into the inner cavity and a plurality vent holes configured to allow air and excess impression material to escape from the inner cavity. Methods of using the impression cap and a dental kit including the impression cap are also disclosed.

5 Claims, 20 Drawing Sheets

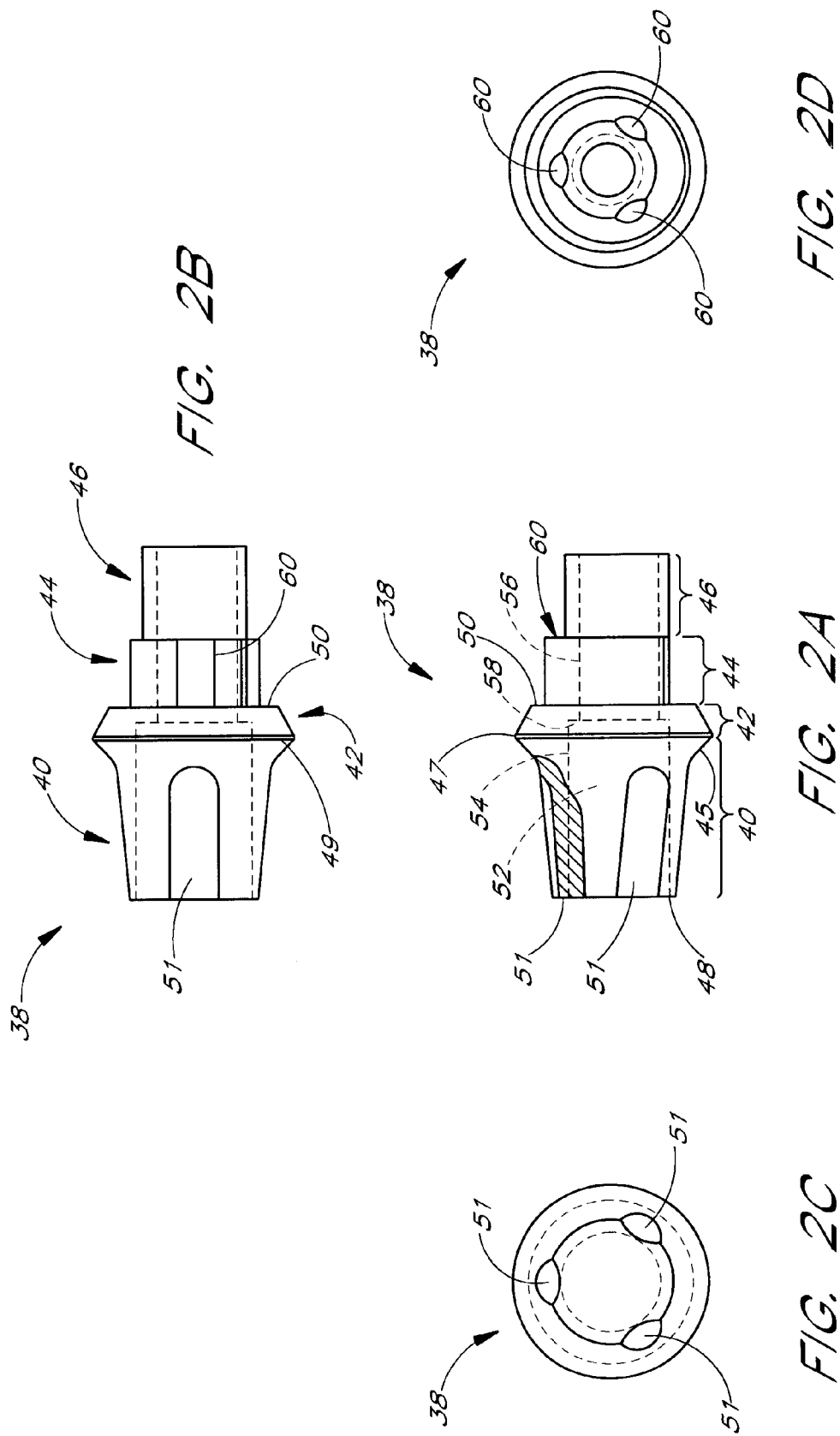

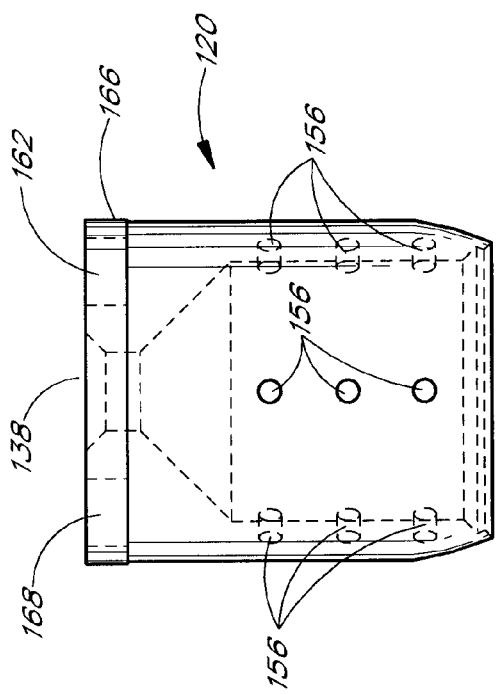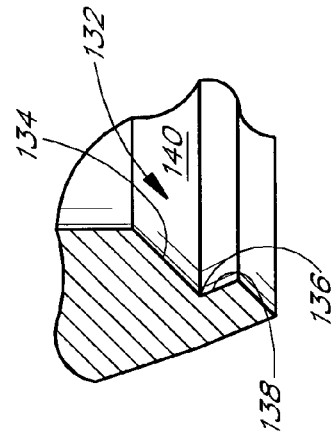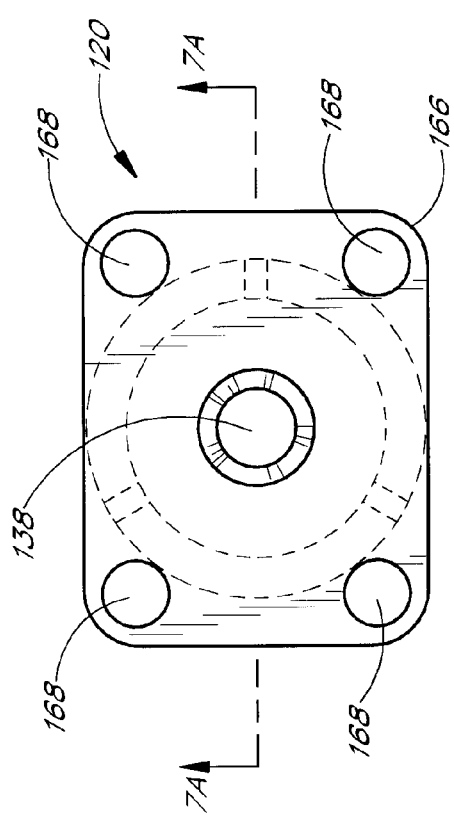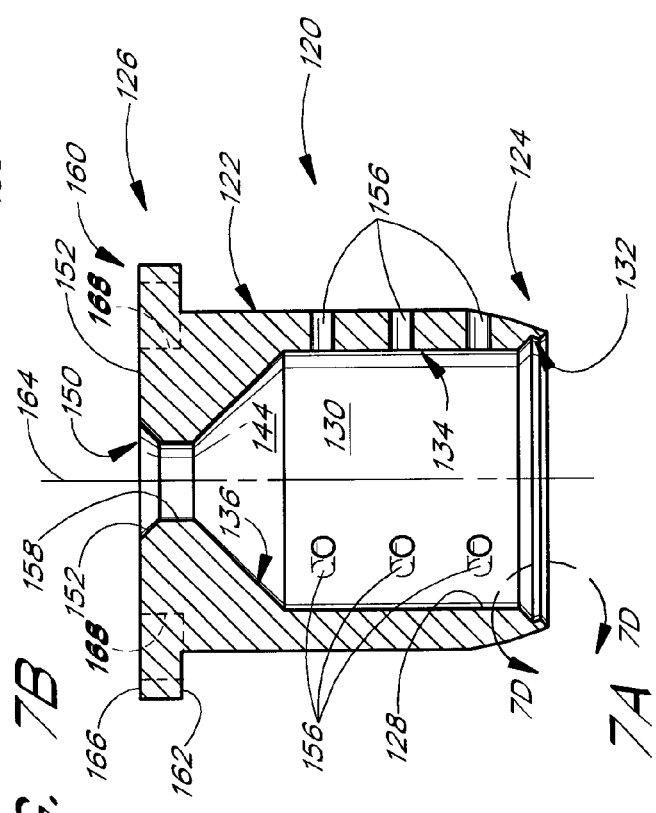

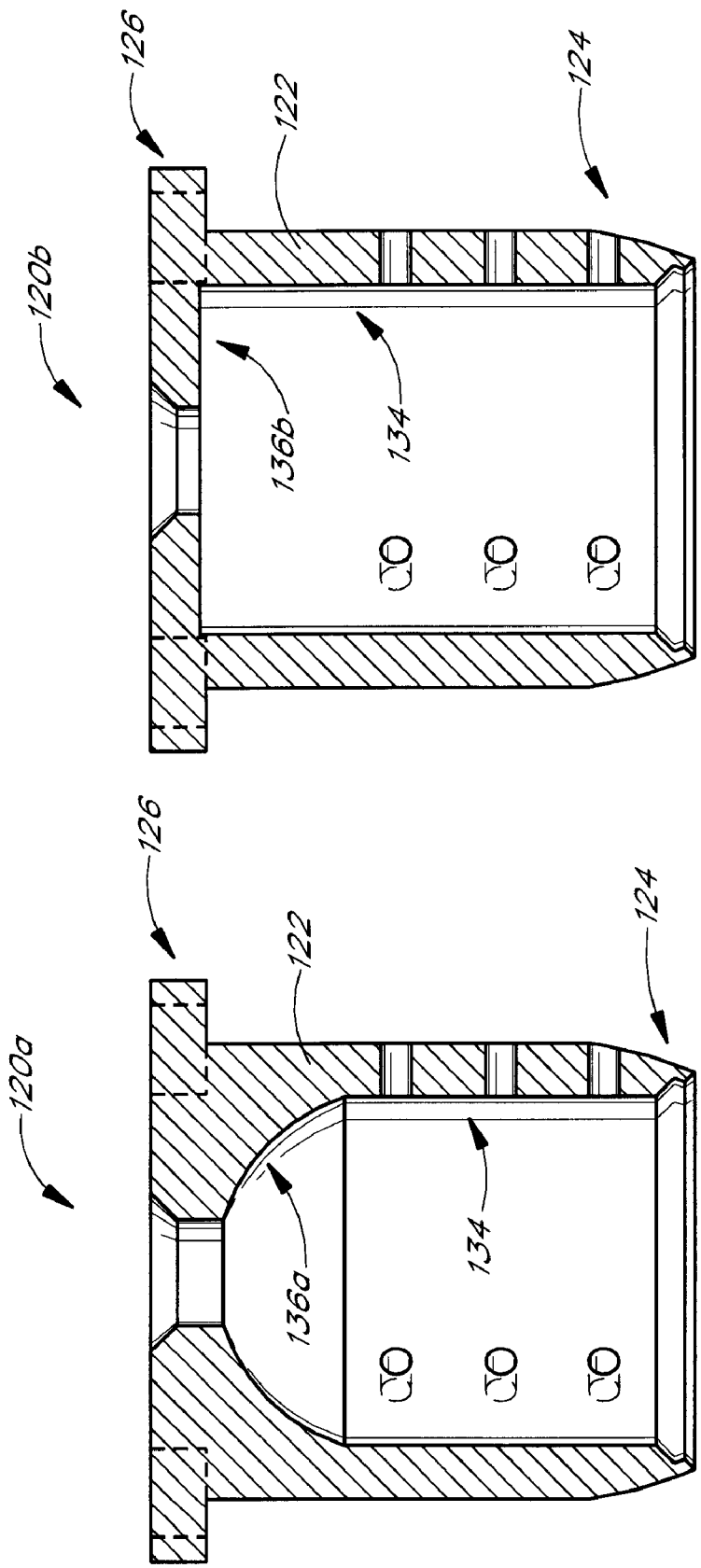

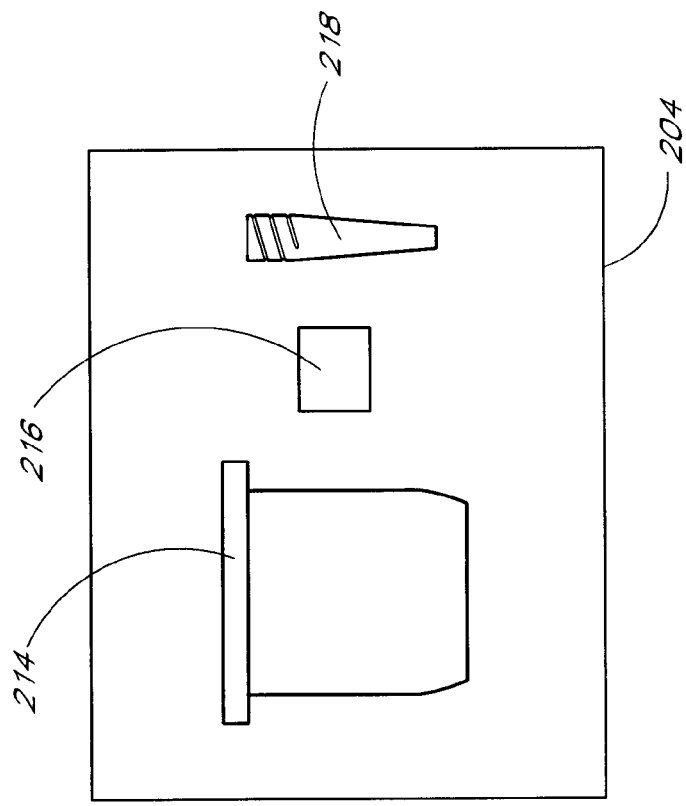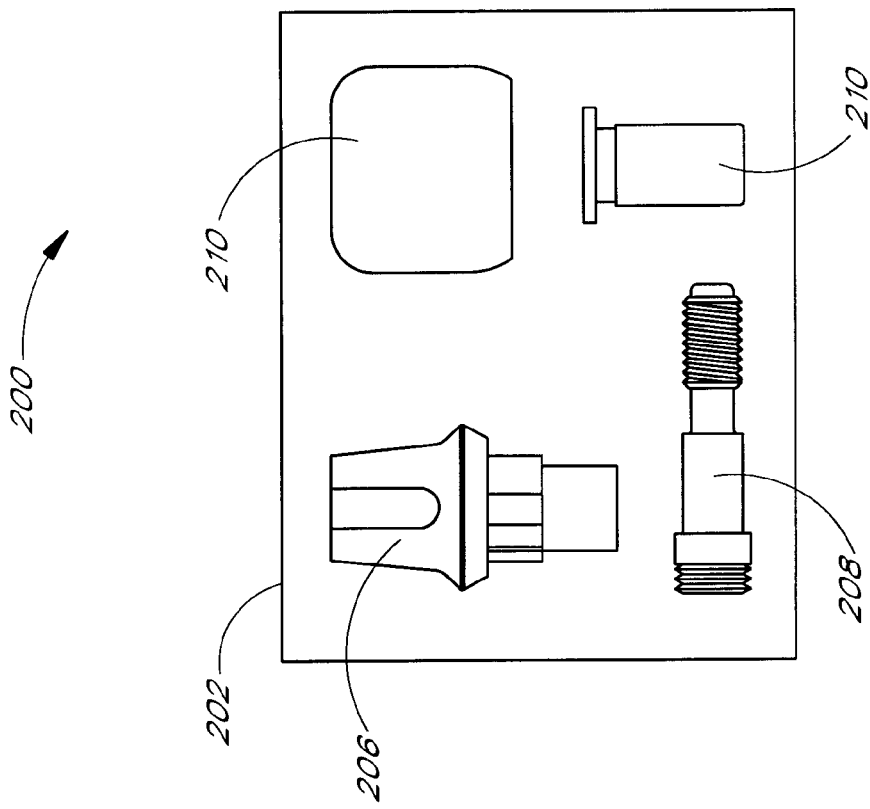
FIG. 16

IMPRESSION CAP

PRIORITY INFORMATION

This invention is based on and claims the benefit of provisional Patent Application No. 60/229,114, filed Aug. 30, 2000, the entire contents of which are hereby expressly incorporated by reference.

BACKGROUND OF THE INVENTION

1. Field of the Invention

The present invention relates generally to dental implants and, more particularly, methods and devices for taking an impression of a final abutment, which is attached to a dental implant.

2. Description of the Related Art

Restoration of an edentulous area of the mouth serves multiple functions, including improved aesthetics, improved mastication, maintenance of crestal bone, and providing for an occlusal stop for a reproducible bite. Restoration can be accomplished using a standard bridge, a removable appliance (a partial or full denture), or a dental implant.

Dental implantation is a procedure for replacing a missing tooth using a dental implant. The placement of the implant is usually accomplished in four stages. In a first stage, a dentist reviews radiographs and dental models to determine the proper placement and axial alignment of the implant. In a second stage, a dental surgeon accesses the bone through the mucosal tissue. With the use of a prefabricated stint, the surgeon drills or bores out the maxillary or mandibular bone. The implant is then either pressed or screwed into the bone. A healing cap is typically then placed over the implant and the surrounding mucosal tissues are sutured over the healing cap. This provides for a biologically closed system to allow osteointegration of bone with the implant. Complete osteointegration typically takes anywhere from four to ten months.

Stage three, involves a second surgical procedure during which the dental surgeon makes an incision in the mucosal tissue to expose the osteointegrated implant. The healing cap is removed and a temporary abutment, having a height at least equal to the thickness of the gingival tissue or a final prosthetic abutment, is coupled to the implant. Once the abutment is secured an immediate mold or impression may be taken. In a modified procedure, the impression may be taken within one to two weeks after the stage three. The impression is used to record the axial position and orientation of the implant, which is then reproduced in a stone or plaster analogue of the patient's mouth. The main objective of the impression is to properly transfer the size and shape of adjacent teeth in relation to the permanently placed implant and the precise configuration and orientation of the abutment to the dental technician. The plaster analogue provides the laboratory technician with a precise model of the patient's mouth, including the orientation of the implant fixture relative to the surrounding teeth. Based on this model, the technician constructs a final restoration. Stage four, in the restorative process, involves replacing the temporary healing abutment with the final restoration.

As noted above, during stage three, a mold or impression is taken of the patient's mouth to accurately record the position and orientation of the implant site and to provide the information needed to fabricate the restorative replacement and/or intermediate prosthetic components. There are several conventional methods for taking the this impression.

One method involves a conventional transfer coping. Transfer copings have an impression portion adapted to form a unique or indexed impression in the impression material and a base portion having mating indexing means adapted to mate with the exposed indexing means of the implant or prosthetic abutment. In use, the transfer coping is temporarily secured to the exposed proximal end of the implant fixture such that the mating indexing means of the impression coping and implant are interlockingly mated to one another. Typically, a threaded screw or bolt is used to temporarily secure the transfer coping to the implant fixture.

Once the impression coping is secured to the implant fixture, an impression of the transfer coping relative to the surrounding teeth is taken. Typically, this involves a "U" shaped tray filled with an impression material that is placed in the patient's mouth over the implant site. The patient bites down on the tray, squeezing the impression material into the implant site and around the transfer coping. Within a few minutes, the impression material cures or hardens to a flexible, resilient consistency. The impression tray is then removed from the patient's mouth to reveal an impression of the implant site and the transfer coping. The restorative dentist then removes the transfer coping from the patient's mouth and transfers the transfer coping back into the impression material, being careful to preserve the proper orientation of the indexing means.

Another method typically involves a conventional pickup coping. Pick-up copings are similar to the transfer copings described above; except that a pick-up coping typically includes an embedment portion adapted to be non-removably embedded within the impression material. Typically, the embedded portion comprises a protuberant "lip" or similar embedment projection at a coronal portion of the coping. This allows for "grabbing" or traction of the impression material as the tray is being removed from the patient's mouth. The pick-up copings are "picked up" and remain in the impression material when the tray is removed from the patient's mouth.

Yet another method for taking an impression involves an impression or transfer cap. Impression or transfer caps are placed over or on the built-up part of the abutment or the implant and remain in the impression material when the tray is removed. There are several different types of transfer caps. One type of transfer cap has a tapered inner surface, which is adapted in form and size to the built-up part or abutment of the implant. This cap has an inner surface, which has indentations or slots, which correspond to indentation or slots present on the abutment. The cap is attached to the abutment with resilient flaps or tongues. An example of such a cap is illustrated in U.S. Pat. No. 5,688,123. A disadvantage to this type of cap is apparent when the abutment is modified in vitro to create axial draw parallel to adjacent teeth and/or implants. If the abutment is modified, the transfer cap may not represent an accurate impression of the abutment because the indentations or slots may have been mechanically removed during the modification. Therefore, this method does not necessarily accurately reproduce the size and shape of a modified abutment.

Additionally, there are transfer caps which are capable of recording modifications in abutments. These caps typically have a large aperture or hole (diameter greater than ⅓ of the area of the axial wall of the cap) in the distal end (occlusally) for placement or injection of impression materials. Moreover, such impression caps have large apertures or holes on the axial walls to allow excess gas and impression material to escape. They may also utilize a sleeve that inserts inside the impression caps to facilitate recording the slots and recesses of an unmodified abutment. A disadvantage of these types of impression caps is that an excessive amount of impression material gets displaced through the large holes or apertures leaving air bubbles and voids, which reduce the accuracy of the impression.

SUMMARY OF THE INVENTION

Accordingly, one aspect of the present invention is an impression cap for taking dental impressions in a patient's mouth. The impression cap comprises a distal end that includes a top surface, a proximal end that defines an opening, and an inner surface that defines an internal cavity. The proximal end of the impression cap is configured to engage a corresponding shoulder of a prosthetic abutment. The impression cap further comprises an injection port configured to receive a tip of an injection syringe for injecting impression material into the inner cavity and a plurality vent holes configured to allow air and excess impression material to escape from the inner cavity.

Another aspect of the present invention is a dental kit for replacing a missing tooth with a dental prosthesis. The dental kit includes an abutment configured to mate with a dental implant, a coupling screw configured to extend through an inner bore of the abutment so as to couple the abutment to the dental implant, a healing cap with an internal cavity configured to fit over the abutment, a healing cap screw configured to couple the healing cap to the abutment, an impression cap configured fit over the abutment cap, the impression cap including an injection port and a plurality of bleed holes, and a syringe tip configured to mate with the injection port of the impression cap.

Yet another aspect of the present invention is a method for taking a dental impression in a patient's mouth comprising providing an impression cap with an injection port and a plurality of vent holes, positioning an impression cap onto a prosthetic abutment; and injecting a first impression material into the impression cap through the injection port until the first impression material is extruded through at least one of the vent holes.

Still yet another aspect of the present invention is a method for taking a dental impression in a patient's mouth. The method comprises the step of providing a first set and a second set of components, the first set including an abutment configured to mate with a dental implant in a patient's mouth, a coupling screw configured to extend through an inner bore of the abutment so as to couple the abutment to the dental implant, a healing cap with an internal cavity configured to fit over the abutment, and a healing cap screw configured to couple the healing cap to the abutment, the second set including an impression cap configured fit over the abutment cap and having an injection port and a plurality of bleed holes and a syringe tip configured to mate with the injection port of the impression cap. The method also comprises coupling the abutment to the dental implant with the coupling screw, coupling the healing cap to the abutment with the healing cap screw; and providing the patient with the second set of components.

Further aspects, features and advantages of the present invention will become apparent from the following description of the preferred embodiments.

BRIEF DESCRIPTION OF THE DRAWINGS

These and other features of the invention will now be described with reference to the drawings of the preferred embodiments, which are intended to illustrate and not to limit the invention, and in which:

FIG. 2A is a side view of one embodiment of a final abutment, which is configured to mate with the dental implant of FIG. 1A or FIG. 1D;

FIG. 2B is another side view of the final abutment of FIG. 2A;

FIG. 2C is a top plan view of the final abutment of FIG. 2A;

FIG. 2D is a bottom plan view of the final abutment of FIG. 2A;

FIG. 7A is a cross-sectional side view of an impression cap having certain features and advantages according to the present invention;

FIG. 7B is a top plan view of the impression cap of FIG. 7A;

FIG. 7C is a side elevational view of the impression cap of FIG. 7A;

FIG. 7D is a close up view of a portion of FIG. 7A;

FIG. 9A is a cross-sectional view of a modified embodiment of an impression cap having certain features and advantages according to the present invention;

FIG. 9B is a cross-sectional view of another modified embodiment of an impression cap having certain features and advantages according to the present invention;

FIG. 16 illustrates a dental kit having certain features and advantages according to the present invention.

DETAILED DESCRIPTION OF THE PREFERRED EMBODIMENTS

Figure 1A:
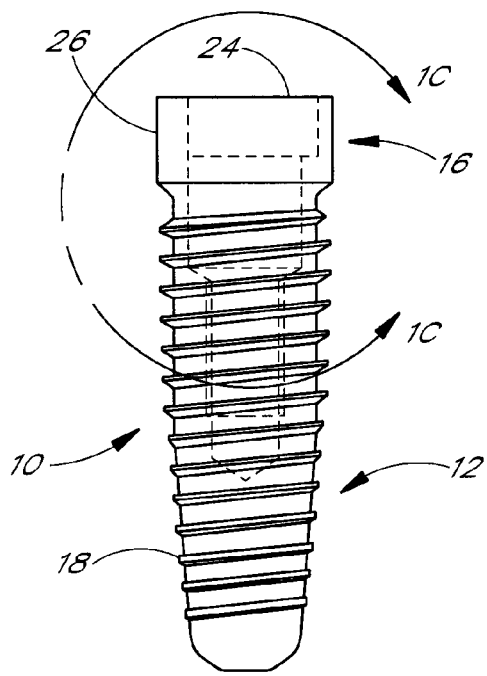
FIG. 1A is a side view of one embodiment of a dental implant.
Figure 1B:
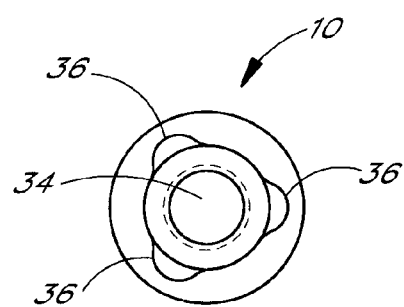
FIG. 1B is a top plan view of part of the dental implant of FIG. 1A.
Figure 1C:
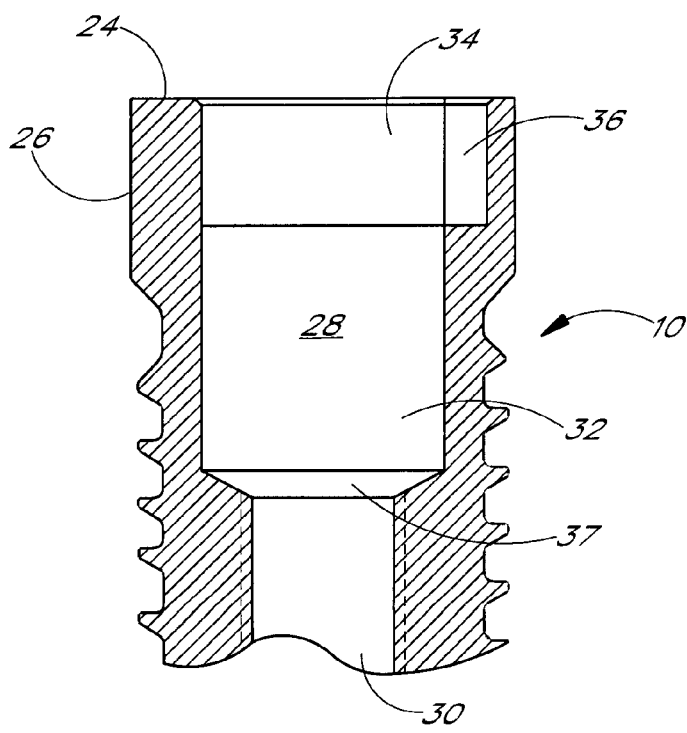
FIG. 1C is a cross-sectional view of the dental implant of FIG. 1A.

The present invention relates primarily to methods and devices that are used to take an impression of various components, such as, for example, a final abutment, which are coupled to a dental implant. FIGS. 1A–1C illustrate one exemplary embodiment of a dental implant 10, which will be used to illustrate certain features and aspects of the present invention. The dental implant 10 is described in detail in co-pending U.S. application Ser. No. 09/670,708, filed Sep. 27, 2000, the disclosure of which is hereby incorporated herein by reference.

Figure 1D:
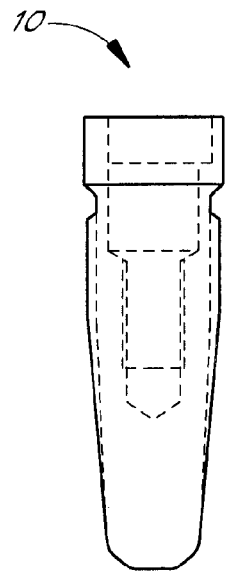
FIG. 1D is a side view of a modified embodiment of a dental implant.

As best seen in FIG. 1A, the implant 10 includes a body portion 12 and a collar 16. The body portion 12 is preferably tapered and includes threads 18 that mate to a preformed threaded hole or osteotomy formed in the patient's jawbone (not shown). However, it should be appreciated that the body portion 12 can also be configured so as to be self-tapping. It should also be appreciated that although the illustrated body portion 12 is tapered or conical, the body portion 12 can be substantially cylindrical. Moreover, in a modified embodiment, the body portion 12 can be unthreaded, as shown in FIG. 1D, if the surgeon prefers to use an unthreaded implant 10. The implant 10 is preferably made of a dental grade titanium alloy, although other suitable materials can also be used.

The collar 16 of the implant 10 is substantially cylindrical and has a top surface 24 that is substantially flat. The collar 16 is defined in part by a vertical side wall 26 that in one embodiment is approximately 2 millimeters in axial length.

As best seen in FIG. 1C, the implant 10 also includes an internal socket 28. The internal socket 28 preferably includes a threaded chamber 30, a post receiving chamber 32, and an anti-rotation chamber 34.

With reference to FIGS. 1B and 1C, the anti-rotation chamber 34 has a central portion having a substantially cylindrical shape. The anti-rotation chamber 34 further includes one or more radially extending portions rotational engagement portions each comprising a channel or lobe 36 extending from the top surface 24 to the bottom of the indexing chamber 34. In the illustrated implant, three engagement portions 36 are provided, each having a substantially half circular shape. As best seen in FIG. 1B, the engagement portions 36 are situated and evenly spaced around the perimeter of the anti-rotation chamber 34. Each engagement portion 36 may be spaced 120 degrees apart from each other channel 36. The anti-rotation chamber 34 is designed to mate with a corresponding anti-rotation region formed on various mating components, such as, for example, a final abutment. The anti-rotation chamber 34 primarily serves to prevent relative rotation between the mating component and the implant 10.

It should be appreciated that in some embodiments the implant 10 does not include the anti-rotation chamber 34. However, the implant 10 preferably includes the anti-rotation chamber 34 because it helps to prevent the relative rotation between the mating components (e.g., a final abutment) and the implant 10. It should also be appreciated that the anti-rotation chamber 36 can be formed into a wide variety of other suitable shapes that may be used with efficacy, giving due consideration to the goals of providing anti-rotation of mating components. For example, the anti-rotation chamber 36 could comprise a hexagonal recess or protrusion that is situated on the top surface 24 of the implant 10. Nevertheless, the illustrated embodiment is preferred because it provides optimal clinical efficacy, ease of use and also minimizes stress concentrations within the anti-rotation chamber 34.

The post-receiving chamber 32 lies between the anti-rotation chamber 34 and the threaded chamber 30. The post-receiving chamber 32 may have a diameter that is less than the diameter of the anti-rotation chamber 36. The post-receiving receiving chamber 32 may include a chamfered region 37, which is adjacent the threaded region 30. As will be explained below, the post-receiving chamber 32 is sized and dimensioned to receive a post that is attached to a mating dental component. The post and the post-receiving chamber 32 provide lateral support, which prevents the mating component from tipping off the implant. However, it should be appreciated that in some embodiments the implant 10 can be formed without the post-receiving chamber 32.

The threaded chamber 30 lies below the post-receiving chamber 32. The threaded chamber 30 is threaded and has a diameter that may be less than the post-receiving chamber 32.

FIGS. 2A–2D illustrate a preferred embodiment of a final abutment 38. The illustrated final abutment 38 is sized and dimensioned to mate with the implant 10 described above. As with the dental implant 10, the final abutment 38 is preferably made of a dental grade titanium alloy, although other suitable materials can be used.

As best seen in FIG. 2A, the outer surface of the final abutment 38 preferably includes an upper region 40, a flared region 42, an anti-rotation region 44, and a post 46. In the preferred embodiment, the upper region 40 is substantially smooth and tapered. The upper region 40 also has a top surface 48 that is substantially flat. Towards the bottom of the upper region (i.e., the portion nearest the flared region 42) is a flared portion 45 that flares outward towards a shoulder or ridge 47. The flared region 42 extends from the shoulder 47 and connects the upper region 40 to a bottom surface 50, which preferably is substantially flat. A margin 49 (see FIG. 2B) defines an interface between the shoulder 47 and the flared portion 45.

The upper region 40 also preferably includes a plurality of grooves 51. These grooves 51 help orient and prevent the rotation of a final restoration (not shown), which typically has an inner surface that matches or engages the shape of the upper region 40 of the final abutment 38. Of course, those skilled in the art will readily appreciate that the upper region 40 and the grooves 51 can be formed into a variety of other shapes that can also provide an anti-rotational interface between the final restoration 54 and the final abutment 38.

It should be appreciated that although the illustrated cross-sections of the upper region 40 and flared region 42 are round in modified arrangements the cross-sections can be non-round. For example, the cross-section of the upper region and flared region can have a non-round cross-section that resembles the cross-section of a natural tooth.

To permanently secure the final restoration, cement can be applied to the upper region 40 of the final abutment 38. Alternatively, the final restoration can be coupled to the final abutment 38 by a screw (not shown). In such an arrangement, a screw hole (not shown) can be provided on the side of the final abutment 38.

As shown in FIG. 2A, the final abutment 38 advantageously includes an inner bore 52 that extends through the center of the final abutment 38. The inner bore 52 is preferably defined by a first and second region 54, 56. The diameter of the first region 54 is preferably slightly larger than the diameter of the second region 56. Accordingly, a seat 58 is formed between the first and second regions 54, 56. The seat 58 supports a coupling screw 62 (see FIG. 3A), which will be described in detail below. Optionally, the second region 56 can include internal capture threads (not shown).

With continued reference to FIG. 2A, the diameter of the bottom surface 50 is preferably approximately equal to the diameter of the top surface 24 of the implant 10. Extending from the bottom surface 50 is the anti-rotation region 44, which is sized and dimensioned to fit within the anti-rotation chamber 36 of the implant. Accordingly, as best seen in FIGS. 2B and 2D, the anti-rotation region 44 is substantially cylindrical and includes three protrusions 60. The protrusions 60 preferably extend along the entire length of the anti-rotation region 44 and have a half circular shape. The protrusions 60 are arranged around the perimeter of the indexing region 44 approximately 120 degrees apart relative to the center axis of the final abutment 38.

As with the anti-rotation chamber 36 of the implant 10, it should be appreciated that the final abutment 38 can be configured without the anti-rotation region 44. However, it is preferred that the abutment 38 include the anti-rotation 44 because it helps to prevent relative rotation between the implant 10 and the final abutment 38. It should also be appreciated that the anti-rotation region 44 can be formed into a wide variety of other suitable shapes that may be used with efficacy to prevent rotation of the implant 10 and the final abutment 38.

Below the indexing region 44 is the post 46. The post 46 is substantially cylindrical and is sized and dimensioned to fit within the post-receiving chamber 32 of the implant 10. As mentioned above, the post 36 provides lateral support to the final abutment 38 when it is placed upon the implant 10. However, it should be appreciated in a modified embodiment the final abutment 38 can be configured without the post 46.

Figure 3A:
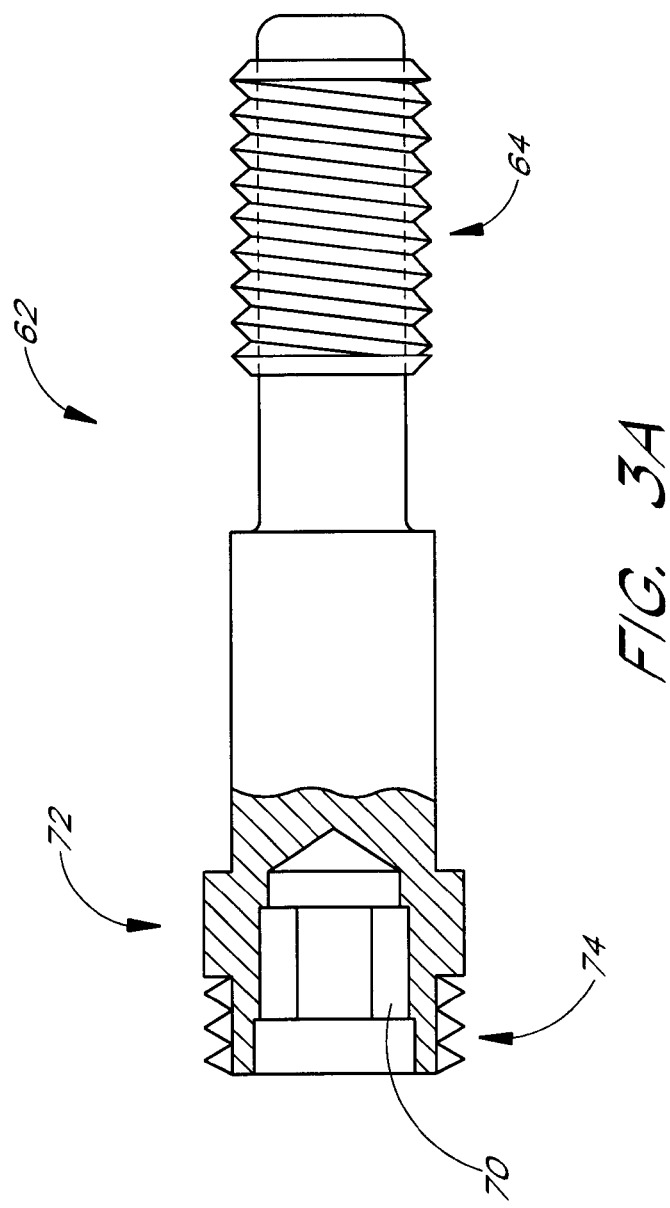
FIG. 3A is a partial cross-sectional side view of one embodiment of a coupling screw.
Figure 3B:
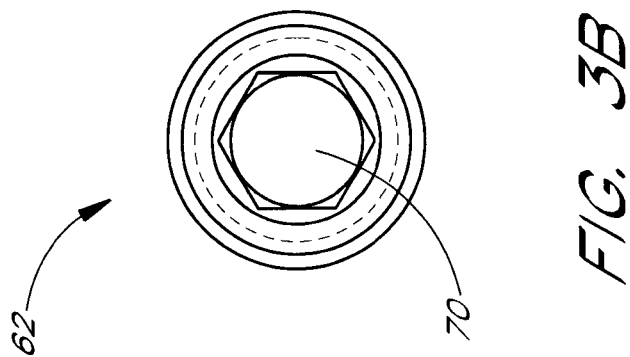
FIG. 3B is a top plan view of the coupling screw of FIG. 3A.

Turning now to FIGS. 3A and 3B, the coupling screw 62 is sized and dimensioned to extend through the inner bore 52 of the final abutment 38 and to couple the final abutment 38 to the implant 10. As with the final abutment 38, the coupling screw 60 is preferably made of a dental grade titanium alloy. However, other suitable materials can be used.

The coupling screw 62 has an externally threaded lower region 64. The threaded lower region 64 is sized and dimensioned to engage the threads of the threaded chamber 30 of the implant 10 (see FIG. 1C). The threaded lower region 64 can also engage capture threads that can be formed on the second region 56 of the final abutment 38. In such an arrangement, the coupling screw 62 engages the capture threads so that the coupling screw 62 does not become disassociated as the final abutment 38 is transferred and fitted to the patient's mouth.

The illustrated coupling screw 62 also advantageously includes a hexagonal recess 70 located within a head 72 of the screw 62. The hexagonal recess 70 allows for the insertion of a hexagonally shaped tool such as a conventional Allen® wrench, which can be used to apply rotational force to the coupling screw 62. The head 72 also advantageously includes outer threads 74, which are formed on the outer surface 75 of the head 72. The purpose and function of the outer threads 74 will be described below. Alternatively, the threads 74 can be formed internally within the recess 70.

In modified embodiments, the final abutment can be coupled to the dental implant in other manners. For example, the final abutment can include configured a threaded post that is adapted to be received within the threaded chamber 30 of the implant 10. One advantage of such an arrangement is that the final abutment can be attached to the implant without a coupling screw.

Figure 4A:
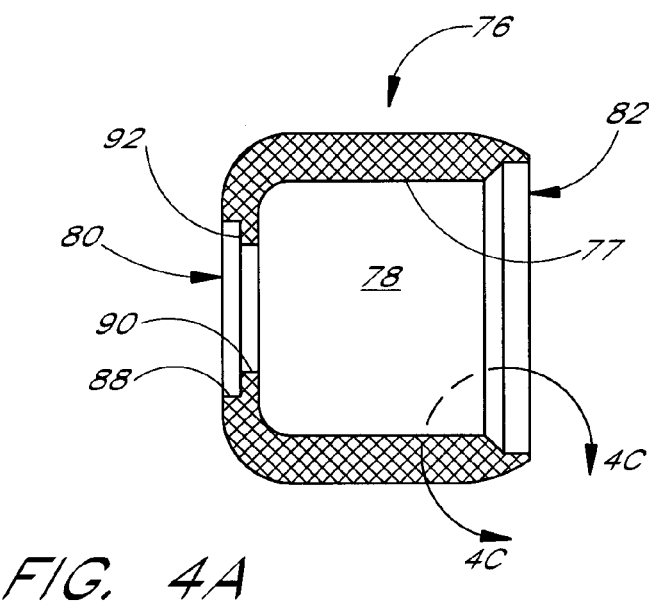
FIG. 4A is a cross-sectional view of one embodiment of a healing cap.
Figure 4B:
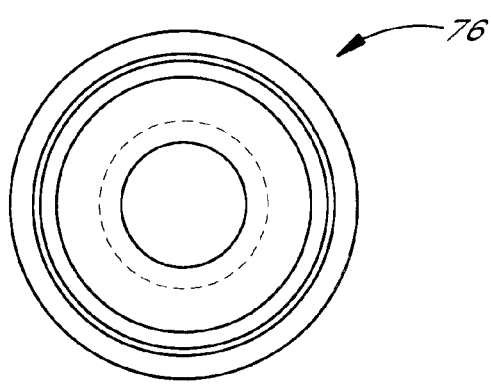
FIG. 4B is a top plan view of the healing cap of FIG. 4A.
Figure 4C:
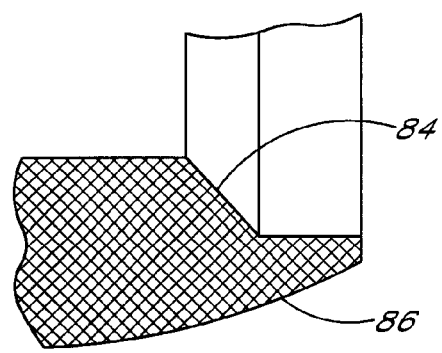
FIG. 4C is a close up view of a portion of FIG. 4A.

FIGS. 4A–4C illustrate one embodiment of a healing cap 76, which can be used to cover the final abutment 38 after, for example, stage two surgery. The healing cap 76 is described in detail in co-pending U.S. patent application Ser. No. 09/853,866, filed May 11, 2001, which is hereby incorporated by reference herein. The healing cap 76 may be made of a synthetic polymer, such as, for example, polyester or Nylon. However, it should be appreciated that other suitable materials can also be used. The healing cap 76 is preferably white or close to natural tooth color so that it has a natural appearance when it is placed in the patient's mouth.

Figure 6:
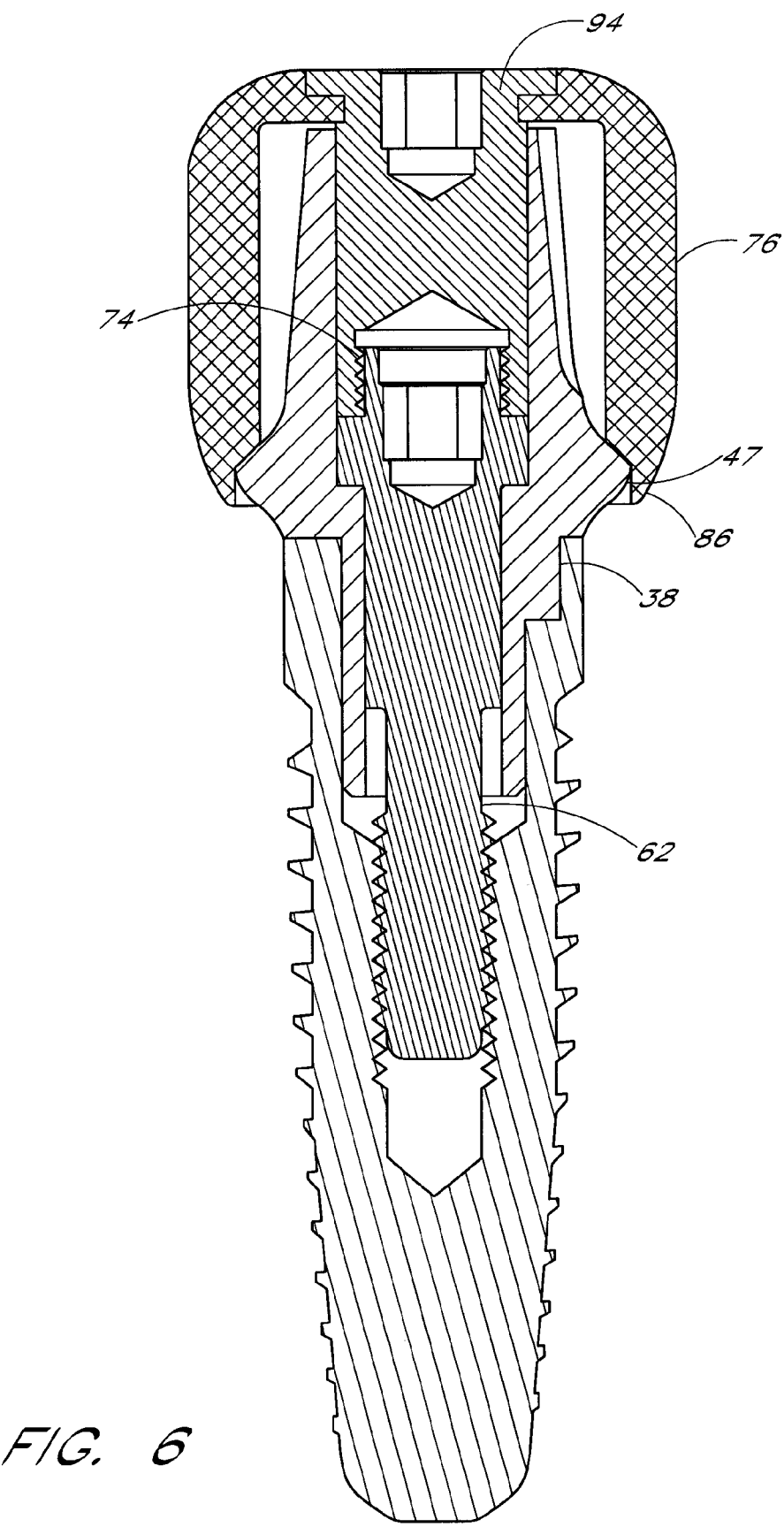
FIG. 6 is a cross-sectional side view of the healing cap of FIG. 4A coupled to the abutment of FIG. 2A, which is attached to the dental implant of FIG. 1A.

The healing cap 76 includes an inner surface 77 which defines an internal cavity 78. The inner surface 77 also defines a top opening 80 and a bottom opening 82. The inner surface 77 is sized and dimensioned such that the that healing cap fits over the upper region 40 of the final abutment 38 as best seen in FIG. 6. With particular reference to FIG. 4C, the inner surface 77 preferably includes a stop for limiting advance of the healing cap 76 onto the abutment 38, such as, a base surface 84 that is sized and dimensioned to rest against the flanged portion 45 of the final abutment 38.

With continued reference to FIG. 4C, the healing cap 76 also preferably includes a tissue retraction flange 86. The tissue retraction flange 86 is sized and dimensioned such that when the healing cap 76 is placed upon the final abutment 38 it extends beyond at least the upper limit of the shoulder 47 of the final abutment 38.

With reference to FIG. 4B, the top opening 80 is preferably defined by top and bottom portions 88, 90. The diameter of the top portion 88 is slightly larger than the diameter of the second portion 90. Accordingly, a seat 92 is formed between the first and second portions 88, 90. The seat 92 provides support for a healing cap screw 94 (see FIGS. 5A–C). Alternatively, and/or in addition, the opening 80 may be flared or chamfered to provide a flared seating surface.

As with the final abutment 38, it should be appreciated that although the illustrated cross-sections of the healing cap 76 are round in modified arrangements the cross-sections can be non-round. For example, the cross-sections can have a non-round cross-section that resembles the cross-section of a natural tooth.

Figure 5C:
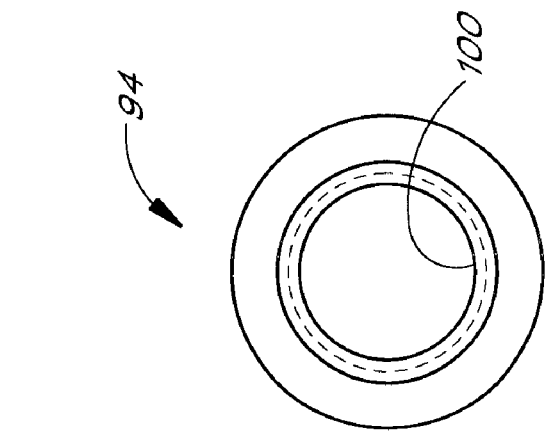
FIG. 5C is a bottom plan view of the healing cap screw of FIG. 5A.
Figure 5A:
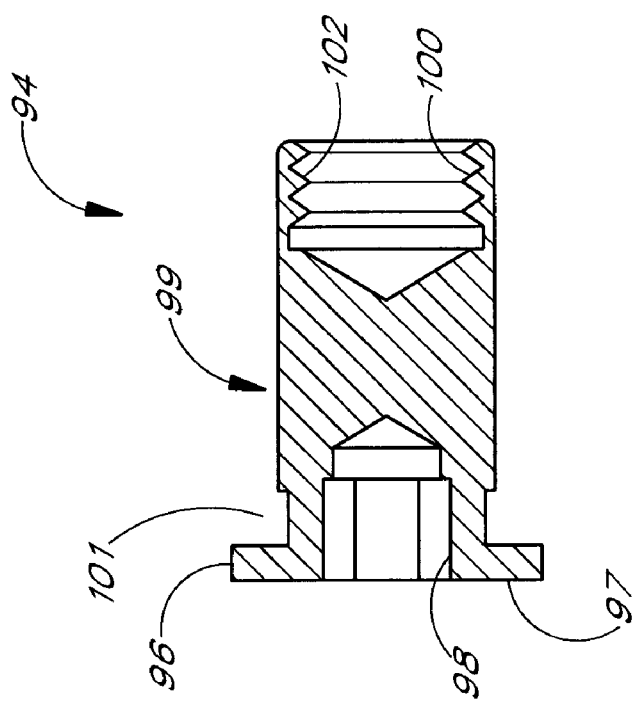
FIG. 5A is a cross-sectional side view of one embodiment of a healing cap screw.
Figure 5B:
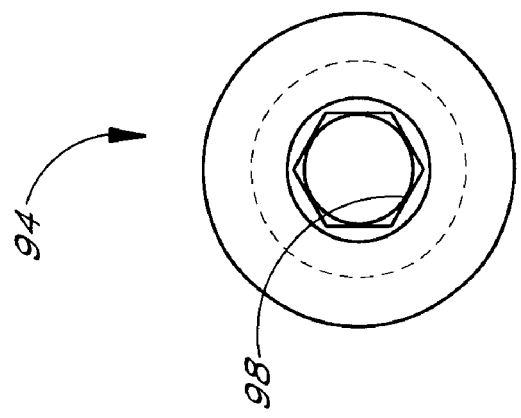
FIG. 5B is a top plan view of the healing cap screw of FIG. 5A.

Turning now to FIGS. 5A–C, the healing cap screw 94 will now be described. The healing cap screw 94 is sized and dimensioned so as extend through the healing cap 76 and to couple the healing cap 76 to the final abutment 38. The healing cap screw 94 is preferably made of a dental grade titanium alloy; although, other suitable materials can be used.

As best seen in FIG. 5A, the healing cap screw 94 includes a flange 96, an upper hexagonal recess 98, a barrel 99 and a lower recess 100. The flange 96 preferably has a diameter that is slightly smaller than the diameter of the upper portion 88 of the healing cap 76. Furthermore, as seen in FIG. 6, the flange 96 is preferably sized and dimensioned such that the top surface 97 of the flange 98 sits flush with the healing cap 76. The hexagonal recess 98 extends through the flange 96 and allows for the insertion of a hexagonally shaped tool such as a conventional Allen® wrench, which can be used to rotate the healing cap screw 94.

The threaded recess 100 is positioned on the lower end of the healing cap screw 94. The threaded recess 100 includes threads 102 that are sized and dimensioned to match the outer threads 74 on the head 72 of the coupling screw 62. Accordingly, as best seen in FIG. 6, the healing cap screw 94 extends through the healing cap 76 and can engage the outer threads 74 of the coupling screw 62.

Preferably, the barrel 99 has a diameter that is slightly larger than the inner diameter of the bottom portion of the healing cap 76. The barrel 99 preferably includes a groove 101, which is located below the flange 96 and has a diameter that is slightly smaller than the inner diameter of the bottom portion 90 of the healing cap. As such, the healing cap screw 94 can be press-fit into the healing cap 76 such that the bottom portion 90 fits into the groove 101 and the top portion 97 is flush with the top of the healing cap 76. In this manner, the healing screw 94 is captured by the healing cap 76 and can rotate freely inside the healing cap 76. Of course, in a modified arrangement, the healing cap screw 94 can be configured without the capture feature.

In use, the surgeon typically first places the implant 10 into the patient's jawbone during stage two surgery. A healing cap (not shown) is placed over the implant. The patient returns home for a first healing period, which is typically four to ten months. In stage three, the surgeon makes an incision to expose the implant 10 and removes the healing cap. The surgeon then couples the final abutment 38 to the implant 10 with the coupling screw 62. The surgeon then places the healing cap 76 over the final abutment 38 and uses the captured healing cap screw 94 to couple the healing cap 76 to the final abutment 38 as shown in FIG. 6. Specifically, the surgeon rotates the healing cap screw 94 so that the inner threads 102 engage the outer threads 74 of the coupling screw 62. Accordingly, the healing cap 76 is held securely against the final abutment 38. The healing cap 76 helps to control the healing and growth of the patient's gum tissue around the implant site. The healing cap 76 also improves the appearance of the patient's mouth and provides the patient with a temporary chewing surface. If desired, the healing cap 76 can also be used to support a temporary restoration and/or may itself be shaped in the form of a temporary restoration.

The patient then returns home for a second healing period. The patient then returns to the surgeon. The surgeon loosens the healing cap screw 94 and removes the healing cap 76 from the final abutment 38. At this point, the surgeon takes the impression of the patient's mouth to record the position, orientation and shape of the final abutment within the mouth. In a modified arrangement, the final abutment 38 can be attached during a traditional stage two surgery. In such an arrangement, an impression of the final abutment 38 can also be made during Stage two before the healing cap 76 is attached to the final abutment 38. In still a modified arrangement, a temporary abutment preferably having a height at least equal to the thickness of the gingival tissue can be used during the first and/or second healing periods.

FIGS. 7A–C illustrate one embodiment of an impression cap 120 having certain features and advantages according to the present invention. As will be explained below, the impression cap 120 can be used to take an impression of a final abutment, such as the one described above. In this manner, the shape of the final abutment and/or the axial position and/or orientation of the final abutment and the implant can be recorded. This information can then be used to construct a final restoration.

Figure 8A:
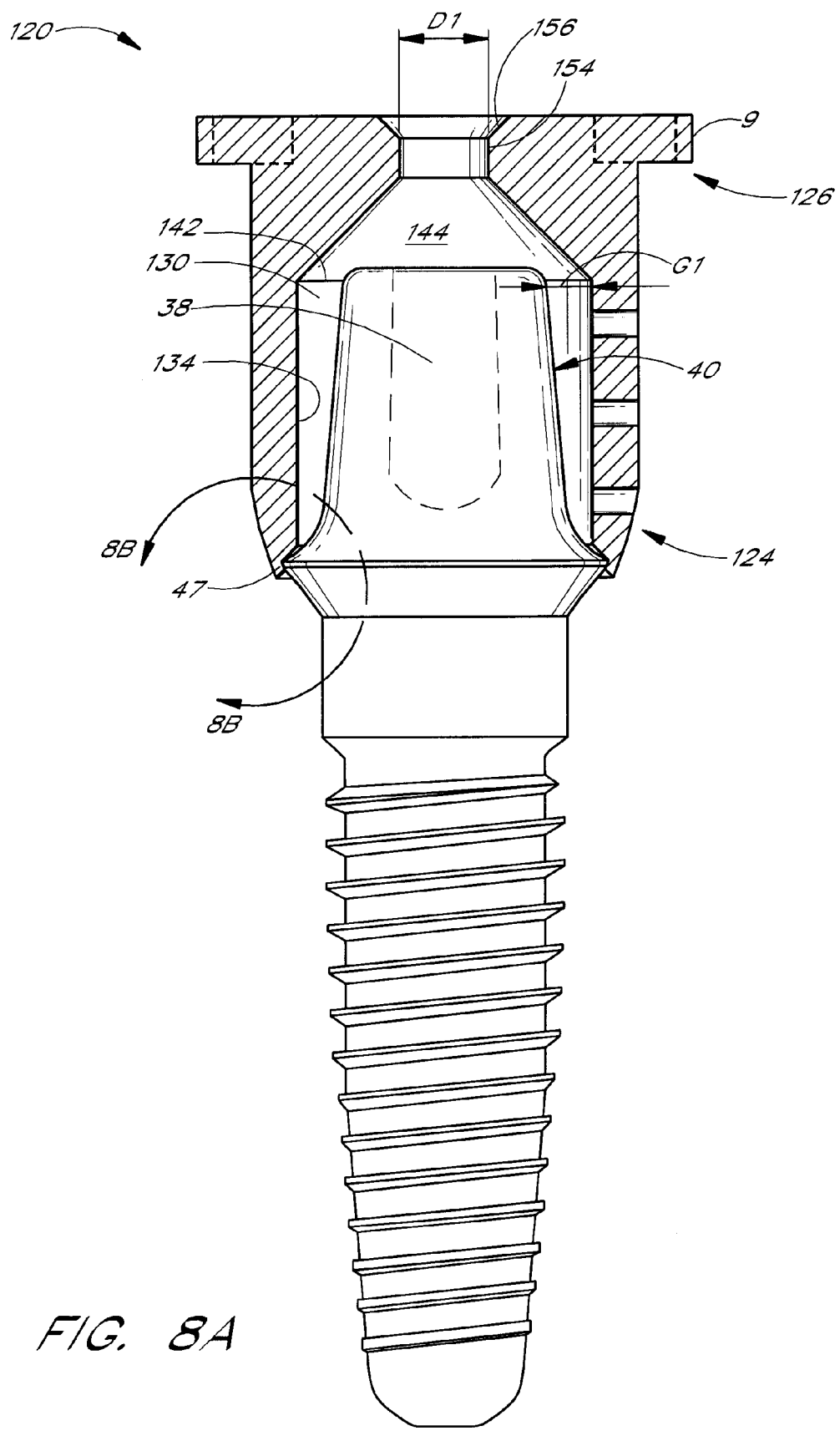
FIG. 8A is a cross-sectional side view the impression cap of FIG. 7A coupled to the abutment of FIG. 2A, which is attached to the dental implant of FIG. 1A.

The illustrated impression cap 120 comprises a body 122 with a proximal end 124 and a distal end 126. The body 122 is preferably made of resilient moldable plastic and/or polymer, such as, for example, polycarbonate. The body 122 defines an inner surface 128, which forms an inner cavity 130. As shown in FIG. 8A, the inner cavity 130 is configured such that the impression cap 100 can fit over the upper region 40 of the final abutment 38. As best seen in FIG. 7A, the inner surface 128 comprises a side wall 134 and roof 136.

Figure 8B:
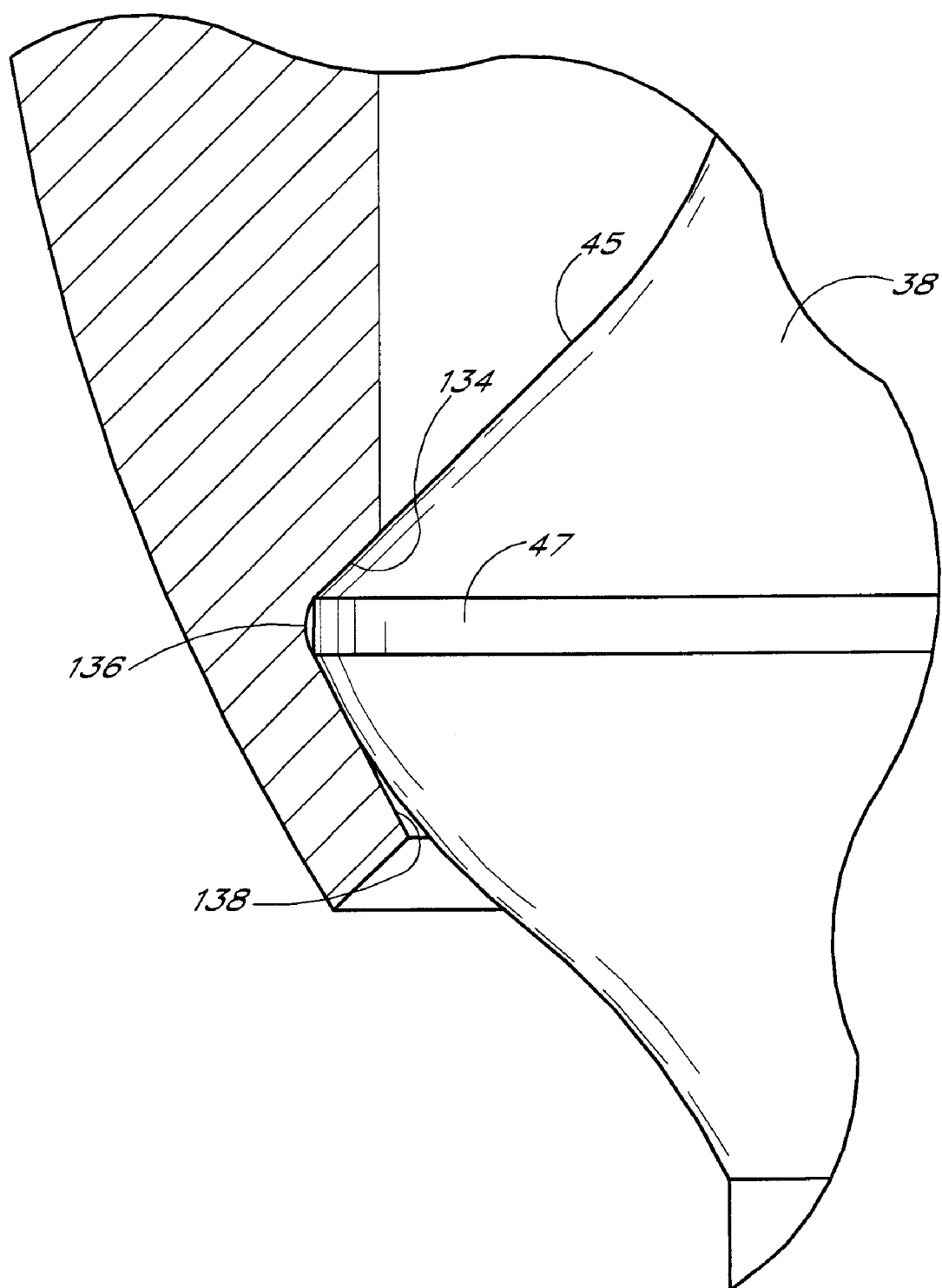
FIG. 8B is a close up view of a portion of FIG. 8A.

The impression cap 120 is preferably configured to engage final abutment 38 in a snap fit. In the illustrated embodiment, this snap fit is achieved by providing the proximal end 124 with a notch or groove 132, which is best seen in FIG. 7D. The groove 132 is configured to snap over the shoulder 47 of the final abutment 38. That is, in the engaged position, the groove 132 fits around the shoulder 47 of the final abutment 10 such that the impression cap 120 is coupled to the final abutment 38. In the illustrated embodiment, the groove 132 is generally V-shaped with an distal portion 134, an apex 136 and a proximal portion 138. In the engaged position, the proximal portion 138 lies generally below the shoulder 47 of the abutment 38, the apex 136 lies generally parallel to the shoulder 47 and the distal portion 134 lies generally above the shoulder 47 (see FIG. 8B). Advantageously, the distal portion 134 is oriented such that it can lie flush with the flared portion 45 of the abutment 38. The distal portion 134 preferably blends into the radius of the apex 136. In one embodiment, the apex 136 has a radius of about 0.004" to 0.002" and, in a preferred embodiment, the apex has a radius of about 0.003".

Preferably, the groove 132 is sized and dimensioned such that in the engaged position the impression cap 120 can be rotated with respect to the final abutment 38. That is, in a preferred embodiment, the space 140 (see FIG. 7D) defined by the groove 132 is slightly larger than the corresponding portions of the flared portion 45, the shoulder 47 and the flared region 42 of the final abutment 38. As such, in the engaged position, the proximal portion 124 of the impression cap 100 is not in a stressed (e.g., in a flexed and/or compressed state). Of course, in one modified embodiment, the groove 132 can be sized and dimensioned such that in the engaged position the proximal portion is stressed and thus exerts a positive holding force on the final abutment 38.

With reference back to FIG. 7A, in the illustrated embodiment, the side wall 134 extends from the proximal portion to the roof 136. As best seen in FIG. 8A, a junction 142 between the side wall 134 and the roof 136 is located at about the same elevation as the top surface of the abutment when the impression cap 120 is in an engaged position. In the illustrated embodiment, the side wall 134 is substantially smooth and has a substantially cylindrical shape. However, in modified embodiments, the side wall 134 can be textured or roughened so as to enhance retention of impression material, which, as will be explained below, is injected into the cavity 130. The substantially cylindrical shape of the side wall 134 is generally preferred because it provides a large amount of space for the impression material near the top surface of the abutment 38, which as will be explained below may be modified by the dental surgeon. Correspondingly, it also provides less space for the impression material near the margin 49 of the abutment 38. This arrangement therefore creates a thin or featheredge of impression material which fades away at the margin 49 of the abutment 38.

In the illustrated embodiment, the roof 136 is funnel shaped. That is, the roof 136 tapers from the most distal end 126 to the side walls 134. Advantageously, the roof 136 defines a transition space 144, which is located above the top surface of the abutment 38 when the impression cap 120 is in the engaged position. The transition space 144 facilitates the flow of impression material above the abutment 38 to the sides and margin 49 of the abutment 38.

FIG. 9A illustrates a modified embodiment of the impression cap 120a wherein like numbers are used to refer to parts similar to those of FIG. 7A. In this embodiment, the roof 136a is domed shaped. FIG. 9B illustrates another modified embodiment of the impression cap 120b wherein like numbers are also used to refer to parts similar to those of FIG. 7A. In this embodiment, the roof 136b is substantially flat. As such, the side walls 134b extends substantially from the distal end 124 to the proximal end 126.

With particular reference to FIG. 7A, the impression cap 120 also includes an injection port 150, which provides a pathway for injecting impression material into the internal cavity 130. In the illustrated embodiment, the injection port 150 is positioned at the distal end 126 on a top surface 152 of the impression cap 120 and communicates with the transition space 144. The illustrated injection port 150 includes a tapered portion 152 and a cylindrical portion 154. With reference to FIG. 8A, the cylindrical portion 154 preferably has a diameter that is approximately equal to a gap G1 between the top of the abutment 38 and the side wall 134. This arrangement is preferred because it ensures that impression material injected into the impression cap is directed towards space between the side of the abutment 134 and the side wall 134. In one embodiment, the cylindrical portion has a diameter of about 0.06 inches and the most distal portion of the tapered section 148 has a diameter of about 0.09.

Figure 10A:
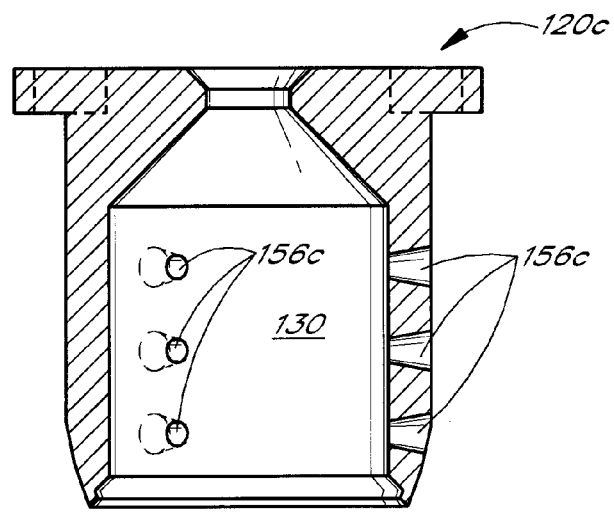
FIG. 10A is a cross-sectional view of a yet another modified embodiment of an impression cap having certain features and advantages according to the present invention.

As best seen in FIGS. 7A and 7C, the impression cap 120 includes a plurality of vent holes 156, which extends through the main body 122 into the cavity 130. In the illustrated embodiment, the vent holes 156 are arranged in three rows. Each row comprises three vent holes 156, which are aligned vertically. The rows are spaced about 120 degrees apart around the periphery of the impression cap 120. As will be explained in detail below, the vent hole 156 provide a vent for air and excess impression material. In one embodiment, the vent holes 156 have a diameter of about 0.2 inches. FIG. 10A illustrates another modified embodiment of an impression cap 120c wherein like numbers are used to refer to parts similar to those of FIG. 7A. In this embodiment, the vent holes 156c are funnel shaped with the end exposed to the inner cavity 130 having a smaller diameter than the other end. As will be explained in detail below, this arrangement enhances the interlocking of the impression cap 120c with the impression material that is injected into the cavity 130.

Figure 10B:
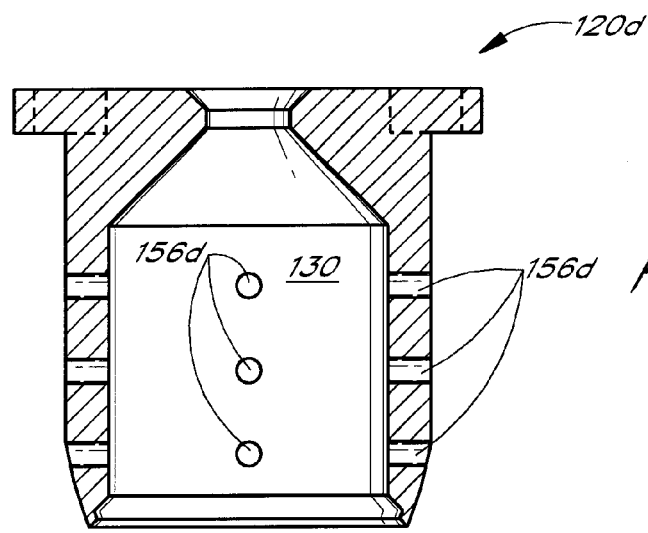
FIG. 10B is a cross-sectional view of still yet another modified embodiment of an impression cap having certain features and advantages according to the present invention.

FIG. 10B illustrates another modified embodiment of an impression cap 120d wherein like numbers are used to refer to parts similar to those of FIG. 7A. In this embodiment, the vent holes 156d are arranged in four rows of three with each row being positioned 90 degrees apart from each other about the perimeter of the impression cap 120d. It should be appreciated that in other embodiments, the impression cap can include more or less than or more than three rows that are arranged symetrically or non-symetrically about the perimeter of the impression cap. In other modified embodiments, each row can include more or less vent holes. In still other modified embodiments, the vent holes can be arranged randomly about the periphery of the impression cap. As mentioned above, the vent holes 156 preferably have a diameter of about 0.02 inches. In modified embodiments, the diameter of the vent holes can be modified giving due consideration to the goal of providing passages for venting air and impression material while still encouraging the impression material to fill the spaces between the abutment 38 and the side wall 134.

With reference back to FIG. 7A, the impression cap 120 preferably includes one ore more embedment features 160. As will be explained in more detail below, the embedment features 160 facilitate the gripping and retention of the impression cap 120 within an impression tray. The one or more embedment features preferably define at least one interference surface 162, which faces lies generally transverse to a longitudinal axis 164 of the impression cap. In the illustrated embodiment, the embedment feature 160 comprises a flange 166, which is positioned the distal end 126 of the main body 122. The illustrated flange 166 includes a plurality of through holes 168 (see also FIG. 7B), which extends through the four corners of the flange 166. Each hole 168 preferably has a diameter of about 0.050".

Figure 11:
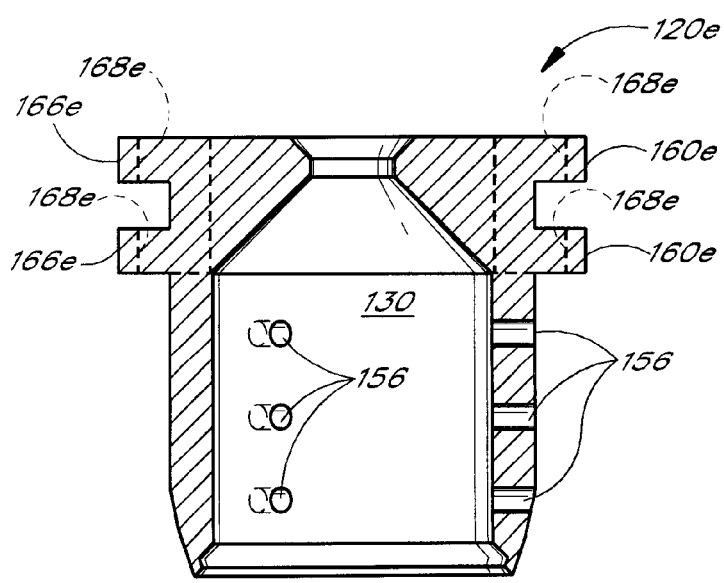
FIG. 11 is a cross-sectional view of another modified embodiment of an impression cap having certain features and advantages according to the present invention.

FIG. 11 illustrates another modified embodiment of an impression cap 120e wherein like numbers are used to refer to parts similar to those of FIG. 7A. In this embodiment, the embedment feature 160e comprises two flanges 166e. Each flange 166e includes four through holes 168e as in the previous embodiment.

It should be appreciated that, although the illustrated embodiments of the impression cap 120 have round cross-sections, in modified arrangements the cross-sections can be non-round.

Figure 12C:
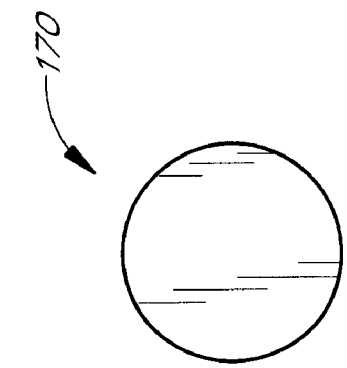
FIG. 12C is a bottom plan view of the block out plug of FIG. 12A.
Figure 12A:
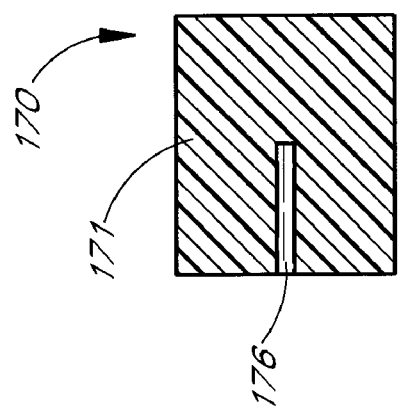
FIG. 12A is a cross-sectional view taken along line 12A—12A of FIG. 12B of a block out plug having certain features and advantages according to the present invention.
Figure 12B:
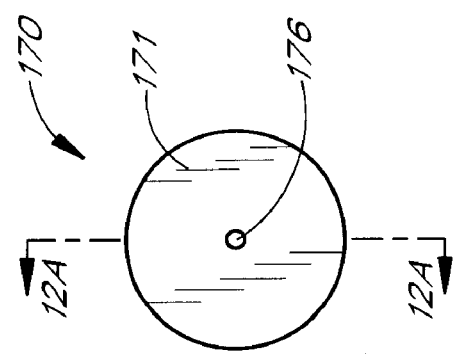
FIG. 12B is a top plan view of the block out plug of FIG. 12A.
Figure 13:
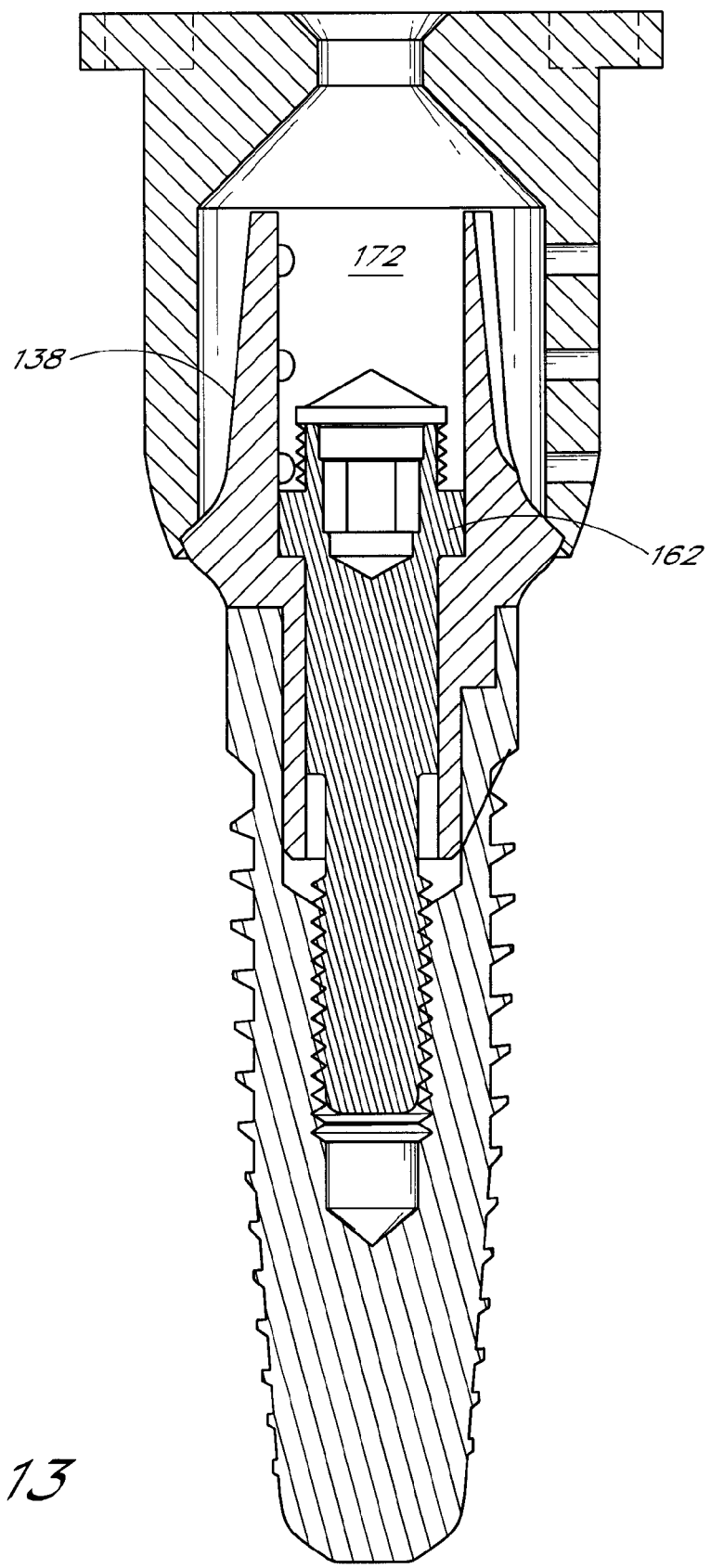
FIG. 13 is a cross-sectional view of the impression cap of FIG. 7A coupled to the abutment of FIG. 2A, which is coupled to the implant of FIG. 1A.

FIGS. 12A–C illustrate a block out plug 170 having certain features and advantages according to the present invention. As will be explained in detail below, the block out plug 170 includes a main body 171 that is sized and dimensioned to prevent impression material from entering a space 172 (see FIG. 13A) in the abutment 38 above the head 72 of the coupling screw 62. The block out plug 170 is preferably made of polyurethane and includes a small hole 176 configured for receiving a dental instrument, such as, for example, a perio probe.

Figure 14A:
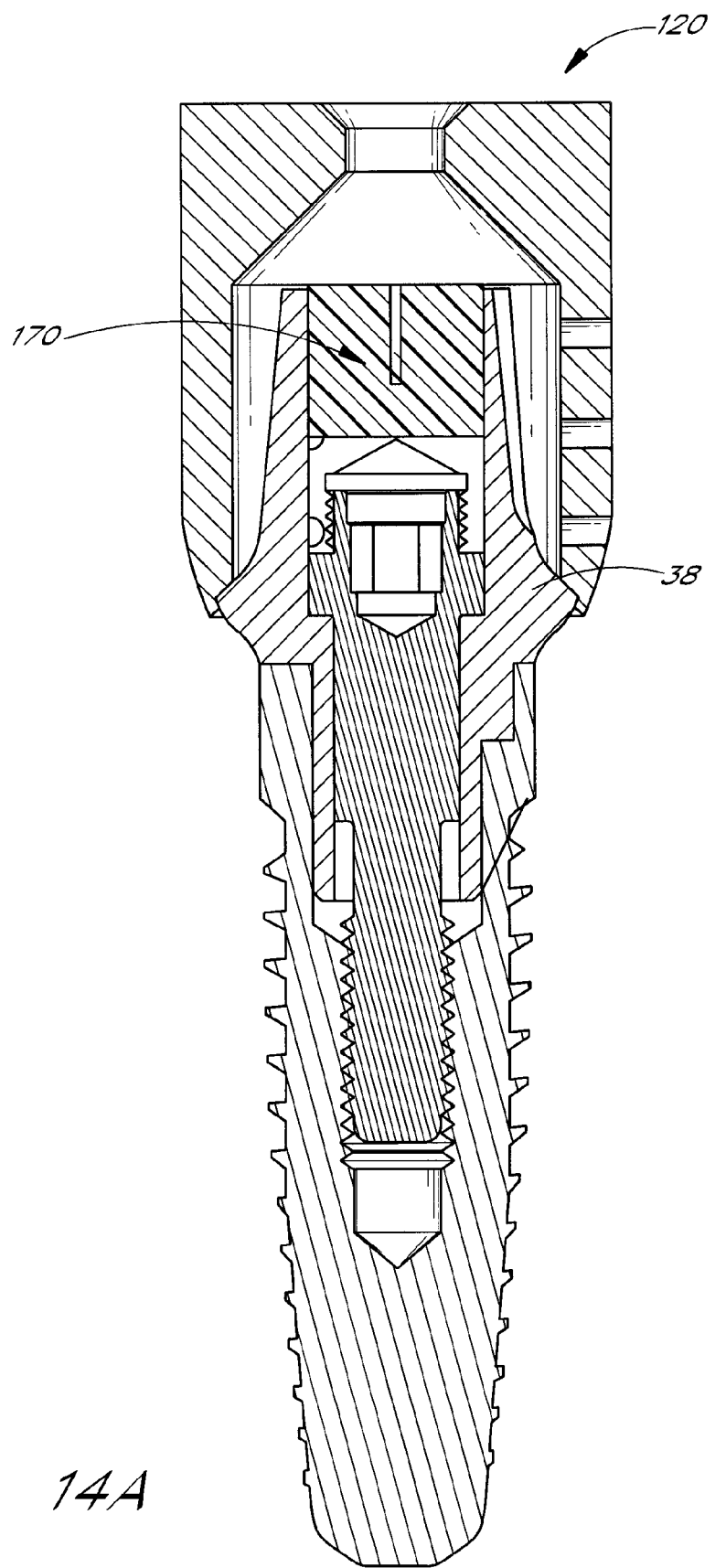
FIGS. 14A–E illustrate a method having certain features and advantages according to the present invention for taking an impression of an abutment.

In use, the impression cap 120 can be used to take an impression of the final abutment 38 and/or record the orientation of the implant 10. Such impression can be taken during stage two or stage three as deemed effective by the dental practitioner. With reference to FIG. 14A, the block out plug 170 is preferably first inserted into the abutment to block out the space 172 above the coupling screw. In the illustrated arrangement, the block out plug 170 can be inserted with a dental instrument, such as, for example a perio probe. In modified arrangements, the block out plug 170 can be inserted by hand. In still other arrangements, the impression cap 120 can be used without the block out plug 170. In such an arrangement, those of skill in the art will recognize that an analog of the abutment 28 should be compensated for the space 172 above the coupling screw 62.

Figure 14B:
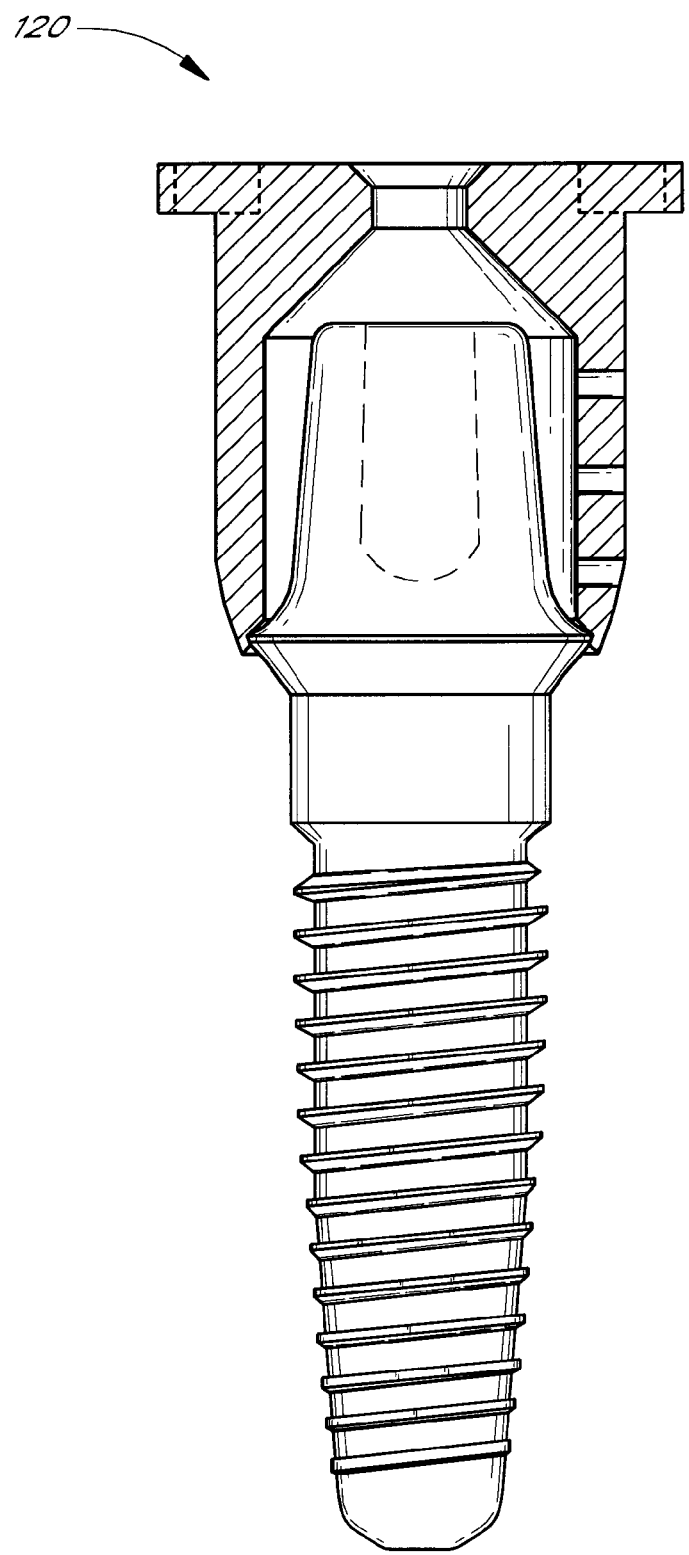
Figure 14C:
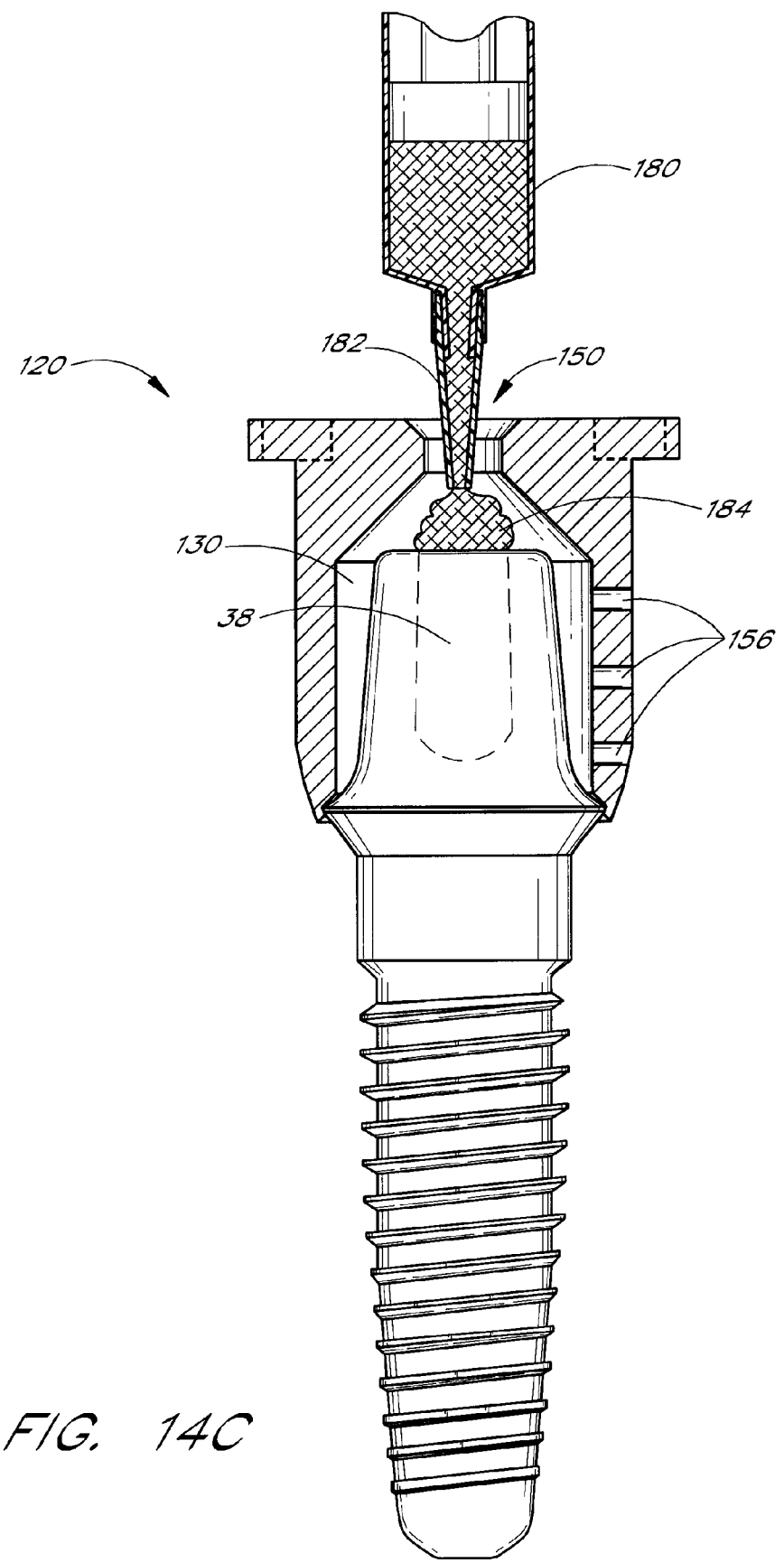

After the block out plug 170 is place, the surgeon then snaps the impression cap 120 onto the abutment 38 as shown in FIG. 14B. After the impression cap 120 is in place, the surgeon uses a syringe 180 (see FIG. 14C) with a small nozzle 182 to inject under pressure a first impression material 184, such as, for example, polyvinylsiloxane or polyether into the cavity 130. Preferably, this involves placing tip 182 of the small nozzle into the internal cavity 130 through the injection port 150.

Figure 14D:
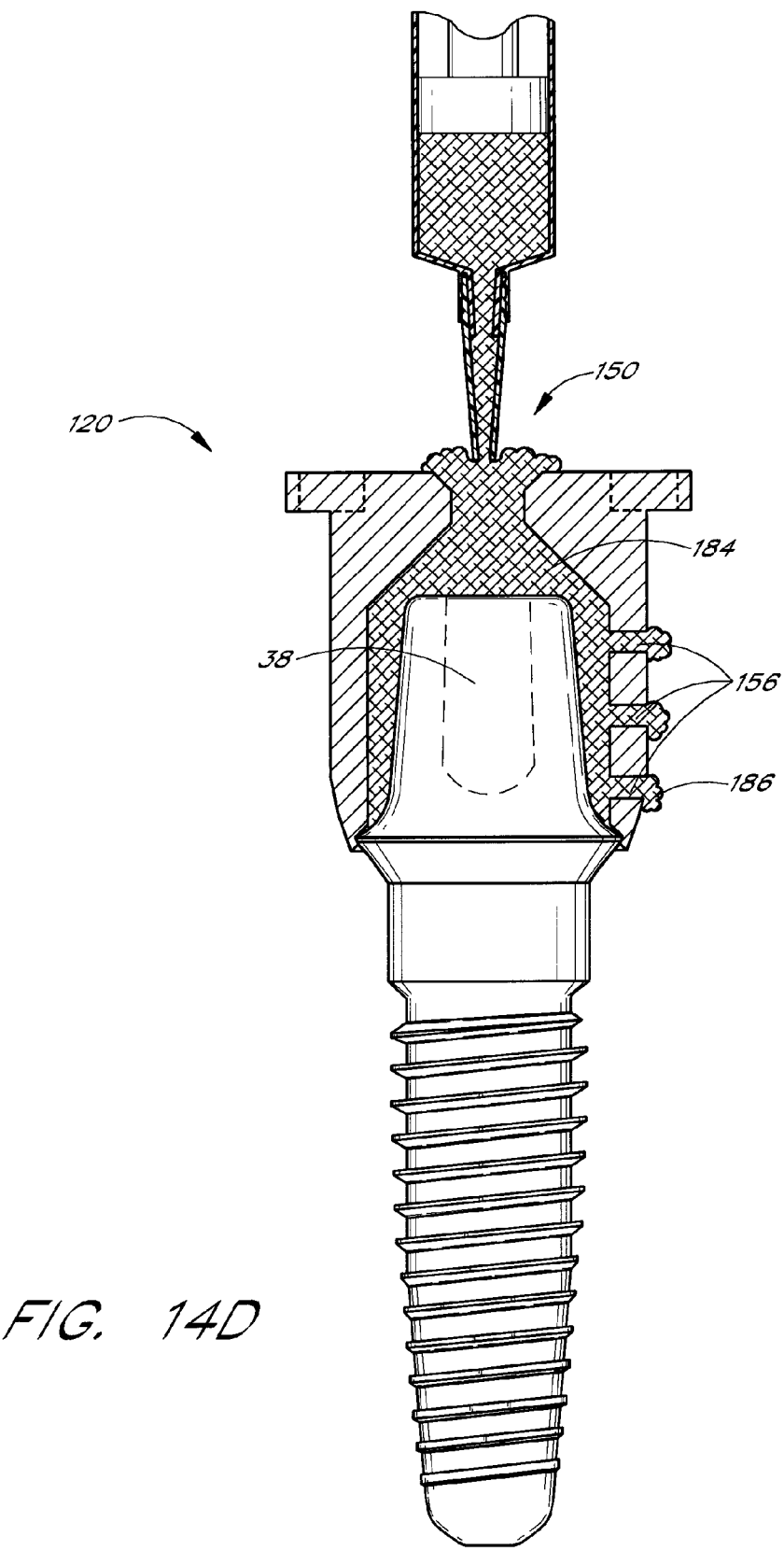

As the impression material is forced into the impression cap 120, air and excess impression material 186 is forced out of the vent holes 156 (see FIG. 14D). Preferably, the surgeon continues to inject impression material 184 into the impression cap 120 until impression material 184 extrudes from most and more preferably all of the vent holes 156. This ensures that the impression material 184 has completely filed the internal cavity 130. As such, the impression material 184 within the impression cap 120 will provide a precise impression of the upper region 40 of the abutment 38 without voids or tears in the impression material 184. The excess material 186 that is forced into the vents 156 becomes locked or trapped within the vents 156. As mentioned above, in some embodiments, the vents 156 are funnel shaped. Advantageously, this increases the interlocking of impression cap 120 with the impression material 184 and helps to prevent separation of the impression material 184 from the impression cap 120.

Figure 14E:
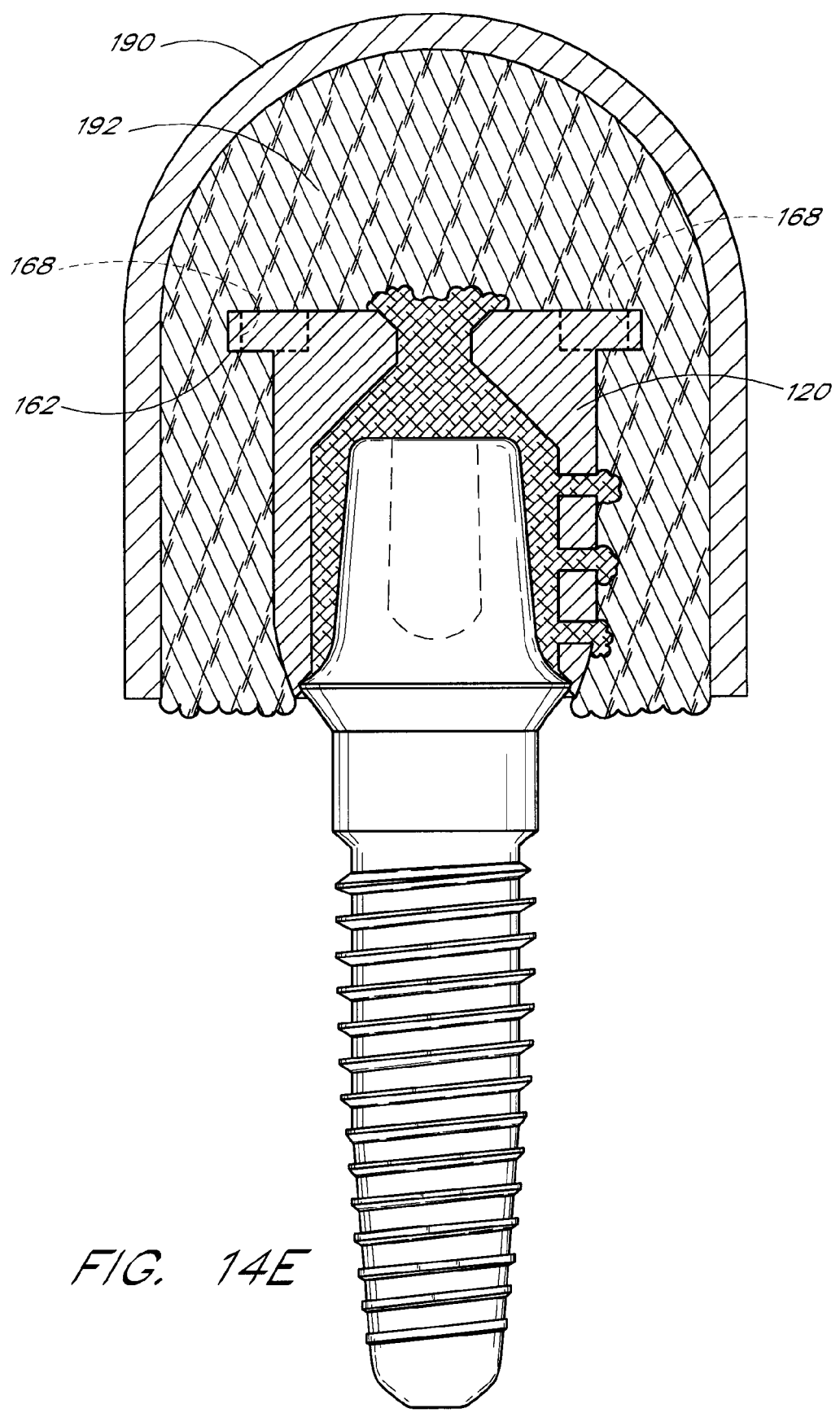

After injecting the impression material into the impression cap 120, an impression is preferably taken of the whole arch or quadrant if the patient's mouth. As shown in FIG. 14E, this typically involves using a U-shaped impression tray 190 that is filled with a second impression material 192. The tray 190 is inserted into the mouth over the impression cap 120. As such, the impression cap 120 becomes embedded in the impression material 192. The interference surface 162 of the impression facilitates mechanically interlocking between the impression material 192 and the impression cap 120. Such interlocking is further enhanced by the holes 168.

Once the second impression material 192 is set, the tray 190 is removed from the mouth. The impression cap 120 remains embedded in the second impression material 192 and is thus uncoupled from the final abutment 38 as the tray 190 is removed. The tray 190 is then sent to a dental laboratory and is used by a dental technician to fabricate a final restoration (i.e., a dental prosthesis). An analog (not shown) of the abutment can be placed within the impression cap, with the same axial orientation as the abutment 38 and the implant 10 in the patient's mouth. The impression tray is then filled or covered with dental stone or any modeling material. After the modeling material has set the model is separated from the impression. The model is an accurate reproduction of the implant site and allows the dental technician to fabricate the final restoration for the patient in the proper position in axial and rotational alignment.

In some instances the dental surgeon may choose to modify the shape of the upper region 40 of the abutment 38. For example, the upper region 40 may be modified to refine the occulusal length and axial draw. By way of example, the upper region 40 may be modified using a high-speed dental handpiece with carbide burs.

Figure 15:
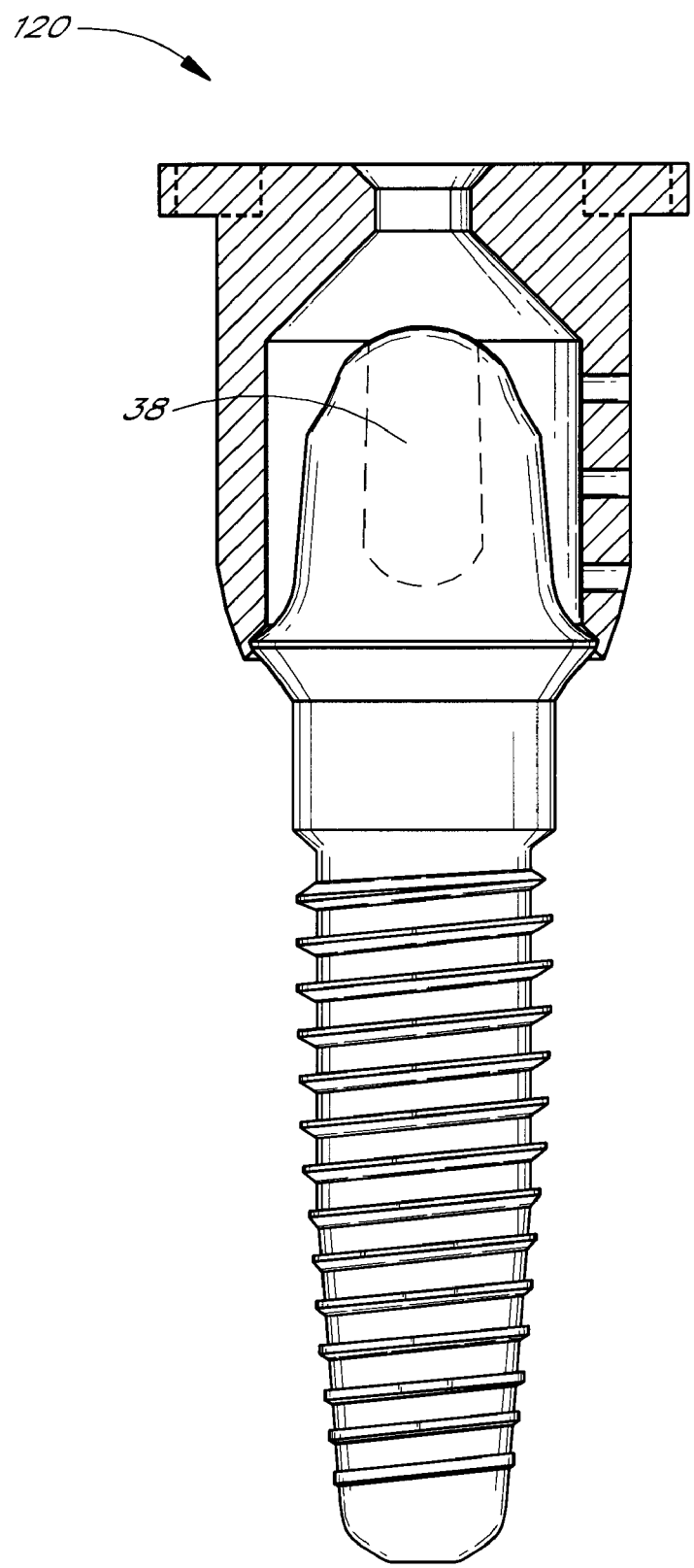
FIG. 15 is a cross-sectional view of the impression cap of FIG. 7A coupled to an abutment that has been modified.

One advantage of the impression cap 120 is that it can be used to record the shape a modified abutment. That is, after the abutment 38 has been modified the impression cap 120 can snapped into place (see FIG. 15). The impression cap 120 is then filled as described above and an impression is taken of the patient's mouth. The impression tray is then sent to a dental laboratory. At the laboratory, the impression cap 120 is filled with dental stone or any modeling material, thereby reproducing the shape of the upper region 40 of the abutment 38, which was stored in the first impression material 184.

FIG. 16 a top plan view of a dental assembly kit 200 having certain features and advantages according to the present invention. In the illustrated embodiment, the kit 200 comprises a first package 202 and a second package 204. The first box preferably contains an abutment 206, the abutment screw 208, a healing cap 210 and a healing cap screw 212, which are preferably arranged as described above. The second package 204 preferably includes an impression cap 214, a block out plug 216 and a syringe tip 218, which are also preferably arranged as described above.

The first and second packages 202, 204 are preferably packaged together in, by way of example, a shrink wrapping. In other arrangements, the contents of the first and second packages can be combined into a single package. In use, the surgeon usually uses the contents of the first package 202 after the implant is uncovered during stage one or stage two. The contents 214, 216, 218 of the second package 204 are advantageously sized and dimensioned to mate with the contents of the first package 202. For example, the impression cap 214 is configured to fit over the abutment 206 and the block out plug 216 is configured to fit into the abutment 206. In a similar manner, the syringe tip 218 is configured to cooperate with an injection port (not shown) of the impression cap 214.

Preferably, the dental surgeon provides the patient with the second package 204 after the abutment 208 has been coupled to the implant. The patient then provides the restorative dentist with the second package 204. In this manner, the restorative dentist has the parts necessary for taking an impression of the abutment 38.

In modified arrangements, the block out plug 216 and/or the syringe tip 218 second package 204 can be omitted from the second package 204. In other arrangements, the healing cap and/or healing cap screw can be omitted from the first package 202.

Although this invention has been disclosed in the context of certain preferred embodiments and examples, it will be understood by those skilled in the art that the present invention extends beyond the specifically disclosed embodiments to combinations, sub-combinations, other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

I claim:

1. A method for taking a dental impression in a patient's mouth comprising the following steps:

providing an impression cap with an injection port and a plurality of vent holes;

positioning an impression cap onto a prosthetic abutment;

injecting a first impression material into the impression cap through the injection port until the first impression material is extruded through at least one of the vent holes; and wherein the step of injecting the first impression material into the impression cap includes inserting a tip of a syringe filled with the first impression material into the injection port of the impression cap.

2. The method of claim 1, wherein the step of positioning the impression cap onto the prosthetic abutment include snapping the impression cap onto a shoulder of the abutment.

3. The method as in claim 1, further including the steps of taking an impression of the patient's mouth by placing an impression tray filed with a second impression material over the impression cap and removing the impression tray and the impression cap from the patient's mouth.

4. The method as in claim 1, further including the step of inserting a block out plug into a space within the prosthetic abutment above a coupling screw.

5. The method as in claim 1, further including modifying the shape of the prosthetic abutment.

* * * * *